US010576128B2

(12) United States Patent
Sigl

(10) Patent No.: US 10,576,128 B2
(45) Date of Patent: Mar. 3, 2020

(54) LIQUID FORMULATION OF A VEGF ANTAGONIST

(71) Applicant: FORMYCON AG, Martinsried/Planegg (DE)

(72) Inventor: Rainer Sigl, Landsberg am Lech (DE)

(73) Assignee: FORMYCON AG (DE)

( * ) Notice: Subject to any disclaimer, the term of this patent is extended or adjusted under 35 U.S.C. 154(b) by 0 days.

(21) Appl. No.: 16/072,638

(22) PCT Filed: Jan. 26, 2017

(86) PCT No.: PCT/EP2017/051662
§ 371 (c)(1),
(2) Date: Jul. 25, 2018

(87) PCT Pub. No.: WO2017/129685
PCT Pub. Date: Aug. 3, 2017

(65) Prior Publication Data
US 2019/0030123 A1 Jan. 31, 2019

(30) Foreign Application Priority Data
Jan. 26, 2016 (EP) ..................... 16152767
Nov. 18, 2016 (EP) ..................... 16199497

(51) Int. Cl.
| | | |
|---|---|---|
| A61K 38/17 | (2006.01) | |
| A61K 9/00 | (2006.01) | |
| A61K 47/02 | (2006.01) | |
| A61K 47/26 | (2006.01) | |
| C07K 14/71 | (2006.01) | |
| A61K 9/08 | (2006.01) | |
| A61P 27/10 | (2006.01) | |
| A61K 47/22 | (2006.01) | |
| C07K 16/22 | (2006.01) | |

(52) U.S. Cl.
CPC .......... *A61K 38/179* (2013.01); *A61K 9/0019* (2013.01); *A61K 9/0048* (2013.01); *A61K 47/02* (2013.01); *A61K 47/22* (2013.01); *A61K 47/26* (2013.01); *A61P 27/10* (2018.01); *C07K 16/22* (2013.01); A61K 9/08 (2013.01); C07K 14/71 (2013.01)

(58) Field of Classification Search
None
See application file for complete search history.

(56) References Cited

U.S. PATENT DOCUMENTS

| | | | |
|---|---|---|---|
| 5,731,144 A | 3/1998 | Toothman et al. | |
| 5,731,424 A | 3/1998 | Toothman et al. | |
| 6,124,449 A | 9/2000 | Gold et al. | |
| 6,207,816 B1 | 3/2001 | Gold et al. | |
| 6,582,959 B2 | 6/2003 | Kim et al. | |
| 6,703,020 B1 | 3/2004 | Thorpe et al. | |
| 9,982,032 B2 * | 5/2018 | Park | C07K 14/71 |
| 2003/0190317 A1 | 10/2003 | Baca et al. | |
| 2013/0323242 A1 * | 12/2013 | Everett | A61K 39/3955 424/134.1 |
| 2015/0157709 A1 * | 6/2015 | Everett | A61K 39/3955 424/134.1 |
| 2015/0182623 A1 * | 7/2015 | Everett | A61K 39/39591 424/134.1 |
| 2016/0297877 A1 | 10/2016 | Sigl | |
| 2017/0232199 A1 | 8/2017 | Fiedler | |
| 2018/0326126 A1 | 11/2018 | Fiedler | |

FOREIGN PATENT DOCUMENTS

| | | |
|---|---|---|
| EP | 0666868 B1 | 4/2002 |
| WO | WO-9410202 A1 | 5/1994 |
| WO | WO-9630046 A1 | 10/1996 |
| WO | WO-9845331 A2 | 10/1998 |
| WO | WO-9845332 A2 | 10/1998 |
| WO | WO-0075319 A1 | 12/2000 |
| WO | WO-2005044853 A2 | 5/2005 |
| WO | WO 2006/104852 * | 10/2006 |
| WO | WO-2006104852 A2 | 10/2006 |
| WO | WO 2007/148334 * | 12/2007 |
| WO | WO-2007149334 A2 | 12/2007 |
| WO | WO-2009155724 A2 | 12/2009 |
| WO | WO-2010060748 A1 | 6/2010 |
| WO | WO-2011135067 A1 | 11/2011 |
| WO | WO-2015071348 A1 | 5/2015 |

OTHER PUBLICATIONS

Adamis, A.P., et al., "Inhibition of Vascular Endothelial Growth Factor Prevents Retinal Ischemia-Associated Iris Neovascularization in a Nonhuman Primate," Archives of Ophthalmology 114(1):66-71, American Medical Association, United States (1996).
Bell, C., "Oligonucleotide NX1838 Inhibits Vegf165-mediated Cellular Responses in Vitro," In Vitro Cellular & Developmental Biology, Animal 35(9):533-542, Springer, Germany (1999).
Chen, Y., et al., "Selection and Analysis of an Optimized Anti-VEGF Antibody: Crystal Structure of an Affinity-matured Fab in Complex with Antigen," Journal of Molecular Biology 293(4):865-881, Academic Press, England (Nov. 1999).
Ferrara, N., et al., "The Biology of Vascular Endothelial Growth Factor," Endocrine Reviews 18(1):1-22, Oxford University Press, United States (1997).
Green, L.S., et al., "Inhibitory DNA Ligands to Platelet-Derived Growth Factor B-Chain," Biochemistry 35(45)14413-14424, American Chemical Society, United States (1996).
Holash, J., et al., "VEGF-Trap: A VEGF Blocker with Potent Antitumor Effects," Proceedings of the National Academy of Sciences USA 99(17):11393-11398, National Academy of Sciences, United States (2002).

(Continued)

*Primary Examiner* — Marianne P Allen
(74) *Attorney, Agent, or Firm* — Sterne, Kessler, Goldstein & Fox P.L.L.C.

(57) ABSTRACT

The present invention relates to liquid pharmaceutical compositions of a VEGF antagonist for intravitreal administration comprising a histidine buffer, an inorganic salt, a carbohydrate and a polysorbate.

14 Claims, 8 Drawing Sheets

(56) References Cited

OTHER PUBLICATIONS

Johnson, D. and Sharma, S., "Ocular and Systemic Safety of Bevacizumab and Ranibizumab in Patients With Neovascular Age-related Macular Degeneration," Current Opinion in Ophthalmology 24(3):205-212, Lippincott Williams & Wilkins, United States (2013).

Jones, A.J., "Analysis of Polypeptides and Proteins," Advanced Drug Delivery Reviews, 10(1):29-90 (1993).

Kajdaniuk, D., et al., "Vascular Endothelial Growth Factor (VEGF)—Part 1: In Physiology and Pathophysiology," Endokrynologia Polska 62(5):444-455, Via Medica, Poland (2001).

Kajdaniuk, D., et al., "Vascular Endothelial Growth Factor (VEGF)—Part 2: In Endocrinology and Oncology," Endokrynologia Polska 62(5):456-464, Via Medica, Poland (2011).

Okamoto, N., et al., "Transgenic Mice With Increased Expression of Vascular Endothelial Growth Factor in the Retina: A New Model of Intraretinal and Subretinal Neovascularization," The American Journal of Pathology 151(1):281-291, Elsevier, United States (1997).

Popkov, M., et al., "Human/mouse Cross-reactive Anti-VEGF Receptor 2 Recombinant Antibodies Selected From an Immune b9 Allotype Rabbit Antibody Library," Journal of Immunological Methods 288(1-2):149-164, Elsevier, Netherlands (2004).

Pearlman and Nguyen, "Analysis of protein drugs," Chapter 6, In Peptide and Protein Drug Delivery, 1st ed., [In Advances in Parenteral Sciences, vol. 4] (Lee, ed.) (Marcel Dekker, Inc., New York, 1991) pp. 247-301.

\* cited by examiner

LIQUID FORMULATION OF A VEGF ANTAGONIST

FIELD OF THE INVENTION

The present invention relates to liquid pharmaceutical compositions of a VEGF antagonist for intravitreal administration comprising a histidine containing buffer, an inorganic salt, a carbohydrate and a polysorbate.

BACKGROUND OF THE INVENTION

Vascular endothelial growth factor (VEGF) is a protein that stimulates vasculogenesis (i.e. de novo formation of new blood vessels) and angiogenesis (i.e. formation of new blood vessels from pre-existing vessels). There are at least six subtypes of VEGF, i.e. VEGF-A, VEGF-B, VEGF-C, VEGF-D, virus VEGF-E and placental VEGF (PlGF). VEGF-A is associated with increases of vascular permeability and degeneration of the extracellular matrix. Four isomers of VEGF-A that arise from alternative splicing of mRNA have been reported in humans (VEGF121, VEGF165, VEGF184, VEGF206) (Ferrara and Davis Smyth, Endocr Rev, 1997, 18:1-22). Further, VEGF110 is produced from VEGF165 by protease cleavage. VEGF-A binds to receptors VEGFr-1 and VEGFr-2 (Kajdaniuk et al., Endokrynol Pol, 2011, 62(5):444-55; Kajdaniuk et al., Endokrynol Pol, 2011, 62(5):456-64).

The specificity of VEGF action for endothelial cells supports a key role in the process of abnormal blood vessel growth and vascular leakage. Anti-VEGF agents have demonstrated efficacy in reducing choroidal neovascularisation in both animal models and clinical trials (Okamoto et al. (1997) Am J Pathol 151: 281-91; Adamis et al. (1996) Arch Ophthalmol, 114: 66-71). Specifically, anti-VEGF antibodies have been used for the treatment of treatments of intraocular neovascular disorders.

Currently available anti-VEGF antibodies are bevacizumab and ranibizumab. Bevacizumab is a full-length, humanized murine monoclonal antibody that recognizes all isoforms of VEGF. Ranibizumab is the Fab fragment of the humanized murine monoclonal antibody that is used to create bevacizumab and has been affinity-matured so that it binds VEGF-A with a significantly higher affinity than bevacizumab. Ranibizumab and bevacizumab appear to have similar efficacy profiles in the treatment of neovascular age-related macular degeneration although rare adverse events seem to occur more often with bevacizumab (Johnson and Sharma, Curr Opin Ophthalmol, 2013, 24(3):205-12).

Another class of VEGF antagonists is represented by fusion proteins of parts of the VEGF receptors and the Fc portion of human immunoglobulins. In particular, aflibercept, marketed under the name Eylea®, is a recombinant fusion protein consisting of the VEGF binding portion from the extracellular domains of human VEGF receptors 1 and 2 that are fused to the Fc portion of the human IgG1 immunoglobulin. It is approved for the treatment of wet macular degeneration and some further ocular diseases.

For medical purposes stable pharmaceutical compositions are of great interest, in particular ready-to-use solutions which require no dissolution or reconstitution before use. A main problem of such a liquid composition is a decreasing content of the active ingredient due to the formation of insoluble particles during repeated freeze/thaw cycles during manufacturing or proteins being degraded and forming degradation products during long-term storage.

WO 2006/104852A2 discloses liquid pharmaceutical formulations of aflibercept for subcutaneous or intravenous delivery which comprise a histidine buffer, sodium chloride, sucrose and polysorbate 20.

In particular for pharmaceutical compositions which are intended to be delivered to the eye, such as pharmaceutical compositions for intravitreal injections, it is important to keep the amount of insoluble particles at a minimum level, since particles may cause irritation or inflammation when injected into the eye.

US 2015/157709 A1 and US 2015/182623 A1 disclose formulations comprising a VEGF antagonist and anti-PDGF aptamer which are suitable for ophthalmological use. These formulations comprise a buffer with pH 5.0 to 8.0 and a tonicity modifier.

WO 2007/149334 A2 describes liquid pharmaceutical compositions of aflibercept comprising a sodium phosphate buffer, sodium chloride, sucrose and polysorbate 20 which formulations are suitable for ophthalmic use.

WO 2015/071348 A1 discloses liquid pharmaceutical formulations of ranibizumab for intravitreal injection comprising a buffer, a non-ionic surfactant, and, optionally, an inorganic salt, wherein the composition does not contain saccharides.

Nevertheless, there is still a need for a pharmaceutical composition which has a low protein aggregate content and is therefore suitable for intravitreal injection and which is stable in liquid form. Preferably, such a composition is suitable for the treatment of AMD and formulated in a prefilled syringe.

SUMMARY OF THE INVENTION

The inventors found that a liquid composition comprising a histidine buffer, a non-ionic surfactant, a VEGF antagonist, an inorganic salt and a carbohydrate has a surprisingly low level of particles and is therefore particularly suitable for intravitreal injection and the treatment of neovascular intraocular diseases.

A further advantage of the liquid pharmaceutical composition used in the present invention is that it does not require a lyophilisation step and is thus produced in a shorter time and with reduced costs. Another advantage is that the composition has a pH in the range of 6.0 to 6.5, i.e. a pH close to the physiological pH.

The object of the present invention is solved by the subject-matter of the independent claims. Preferred embodiments are apparent from the dependent claims.

Accordingly, in one embodiment the present invention provides a liquid pharmaceutical composition for use in the treatment of an intraocular neovascular disease comprising
  a) a histidine containing buffer,
  b) a non-ionic surfactant,
  c) a VEGF antagonist,
  d) an inorganic salt, and
  e) a carbohydrate.

The pH of the composition may be between 6.0 and 6.5, preferably between 6.2 and 6.5. Also preferably, the pH is 6.2 or 6.5.

The histidine-containing buffer may be L-histidine/histidine hydrochloride and/or may be present in a concentration of from 1 mM to 40 mM, preferably of 10 mM.

The non-ionic surfactant may be polysorbate 20 and/or may be present in a concentration of from 0.01 to 0.08% (w/v), preferably of 0.03% (w/v).

The inorganic salt may be NaCl and/or may be present in a concentration of from 20 to 100 mM, preferably of 40 mM.

The VEGF antagonist may be an anti-VEGF antibody or an antigen-binding fragment of such antibody or a VEGF receptor fusion protein, preferably it may be aflibercept or ranibizumab.

The VEGF antagonist may be present in a concentration of 6 to 45 mg/ml.

The carbohydrate may be sucrose and/or may be present in a concentration of 3-20% (w/v), preferably of 5% (w/v).

The present invention also relates to a liquid pharmaceutical composition for use in the treatment of an intraocular neovascular disease consisting of histidine hydrochloride/L-histidine, polysorbate 20, NaCl, aflibercept, sucrose and water and having a pH of 6.2 or 6.5.

The present invention also relates to a liquid pharmaceutical composition for use in the treatment of an intraocular neovascular disease consisting of histidine hydrochloride/L-histidine, polysorbate 20, NaCl, aflibercept, sucrose and water and having a pH of 6.2.

The present invention also relates to a liquid pharmaceutical composition for use in the treatment of an intraocular neovascular disease consisting of histidine hydrochloride/L-histidine, polysorbate 20, NaCl, aflibercept, sucrose and water and having a pH of 6.5.

Preferably, the liquid pharmaceutical composition consists of 10 mM histidine hydrochloride/L-histidine, 0.03% polysorbate 20 (w/v), 40 mM NaCl, 40 mg/ml aflibercept, 5% sucrose and water and has a pH of 6.2 or 6.5.

Also preferably, the liquid pharmaceutical composition consists of 10 mM histidine hydrochloride/L-histidine, 0.03% polysorbate 20 (w/v), 40 mM NaCl, 40 mg/ml aflibercept, 5% sucrose and water and has a pH of 6.2.

Also preferably, the liquid pharmaceutical composition consists of 10 mM histidine hydrochloride/L-histidine, 0.03% polysorbate 20 (w/v), 40 mM NaCl, 40 mg/ml aflibercept, 5% sucrose and water and has a pH of 6.5.

The present invention also relates to a liquid pharmaceutical composition consisting of 10 mM histidine hydrochloride/L-histidine, 0.03% polysorbate 20 (w/v), 40 mM NaCl, 40 mg/ml aflibercept, 5% sucrose and water and having a pH of 6.2 or 6.5.

The present invention also relates to a liquid pharmaceutical composition consisting of 10 mM histidine hydrochloride/L-histidine, 0.03% polysorbate 20 (w/v), 40 mM NaCl, 40 mg/ml aflibercept, 5% sucrose and water and having a pH of 6.2.

The present invention also relates to a liquid pharmaceutical composition consisting of 10 mM histidine hydrochloride/L-histidine, 0.03% polysorbate 20 (w/v), 40 mM NaCl, 40 mg/ml aflibercept, 5% sucrose and water and having a pH of 6.5.

The present invention also relates to a liquid pharmaceutical composition consisting of 10 mM histidine hydrochloride/L-histidine, 0.03% polysorbate 20 (w/v), 40 mM NaCl, a recombinant protein, 5% sucrose and water and having a pH of 6.2 or 6.5.

The present invention also relates to a liquid pharmaceutical composition consisting of 10 mM histidine hydrochloride/L-histidine, 0.03% polysorbate 20 (w/v), 40 mM NaCl, a recombinant protein, 5% sucrose and water and having a pH of 6.2.

The present invention also relates to a liquid pharmaceutical composition consisting of 10 mM histidine hydrochloride/L-histidine, 0.03% polysorbate 20 (w/v), 40 mM NaCl, a recombinant protein, 5% sucrose and water and having a pH of 6.5.

The intraocular neovascular disease may be age-related macular degeneration (AMD), visual impairment due to diabetic macular oedema (DME), visual impairment due to macular oedema secondary to retinal vein occlusion (branch RVO or central RVO), or visual impairment due to choroidal neovascularisation (CNV) secondary to pathologic myopia.

The present invention also relates to a prefilled syringe containing the pharmaceutical composition as defined herein.

BRIEF DESCRIPTION OF THE DRAWINGS

Exemplary embodiments of the invention will be described in the following with reference to the following drawings.

b) Analysis of samples stored at 5° C. for one or three months.

c) Analysis of samples stored at 25° C./60% relative humidity for two weeks, one, two or three months.

d) Analysis of samples stored at 40° C./75% relative humidity for two weeks, one, two or three months.

Figure 1A:
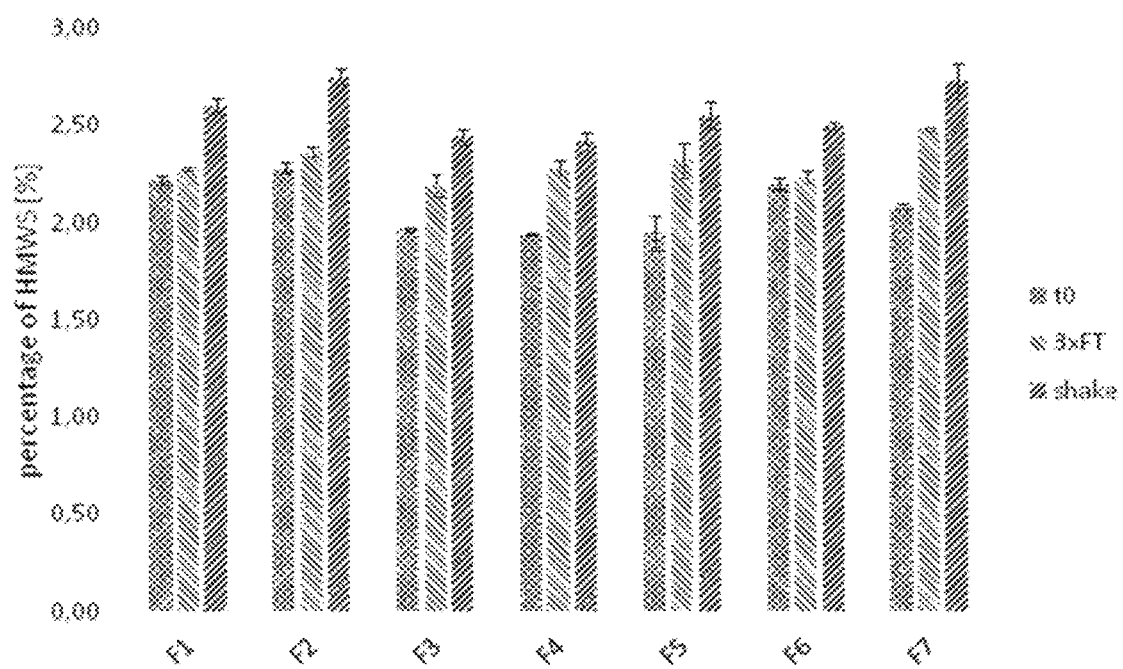
FIG. 1: Detection of high molecular weight species by size exclusion chromatography with samples F1 to F7 subjected to different conditions a) Analysis of samples subjected to stress conditions (three freeze/thaw cycles or shaking for seven days).
Figure 1B:
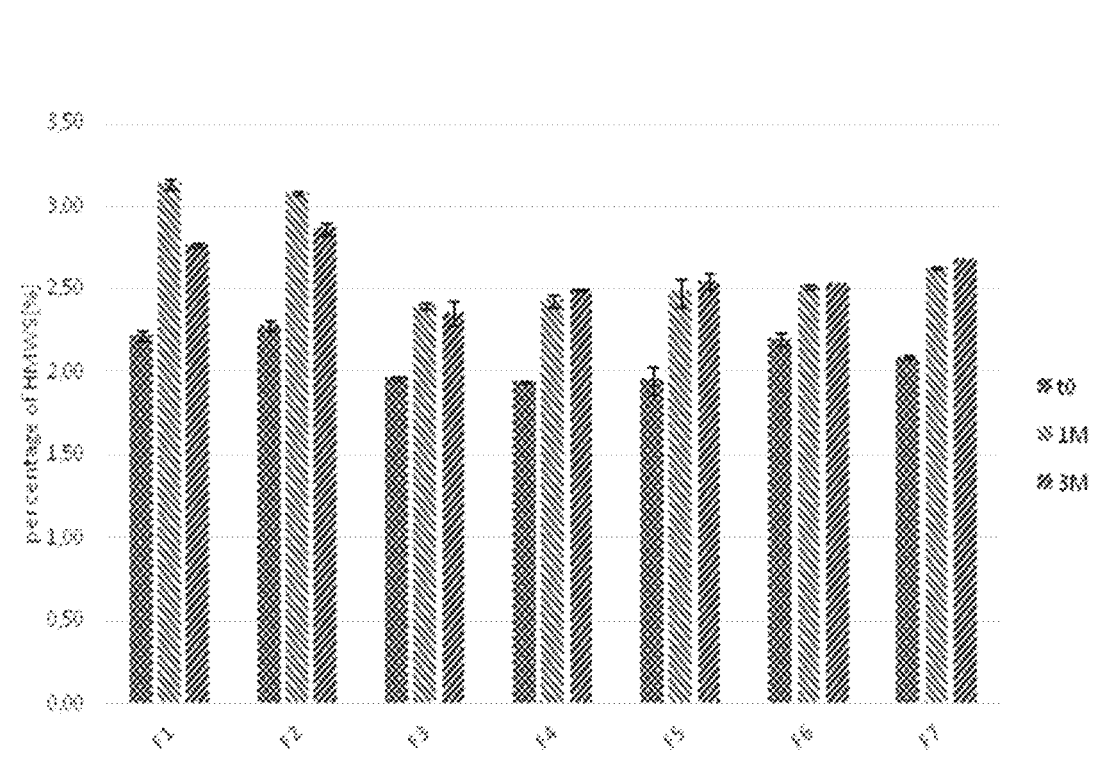
Figure 1C:
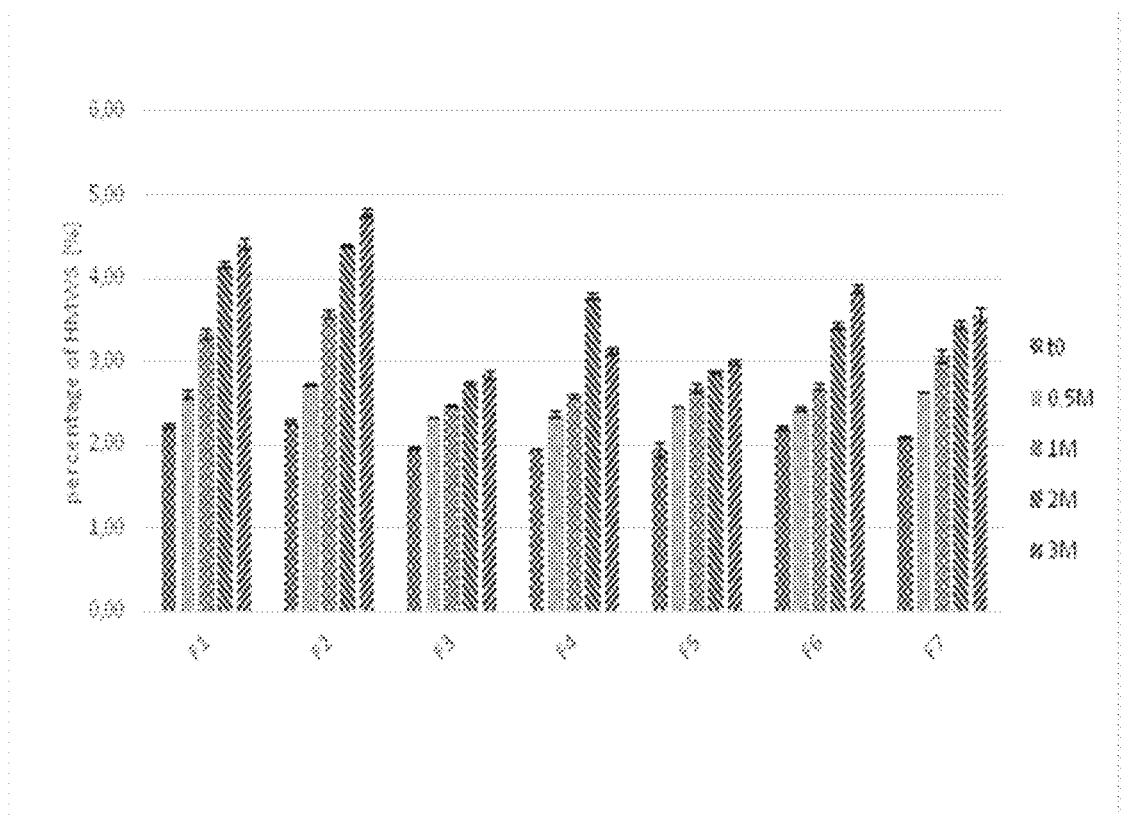
Figure 1D:
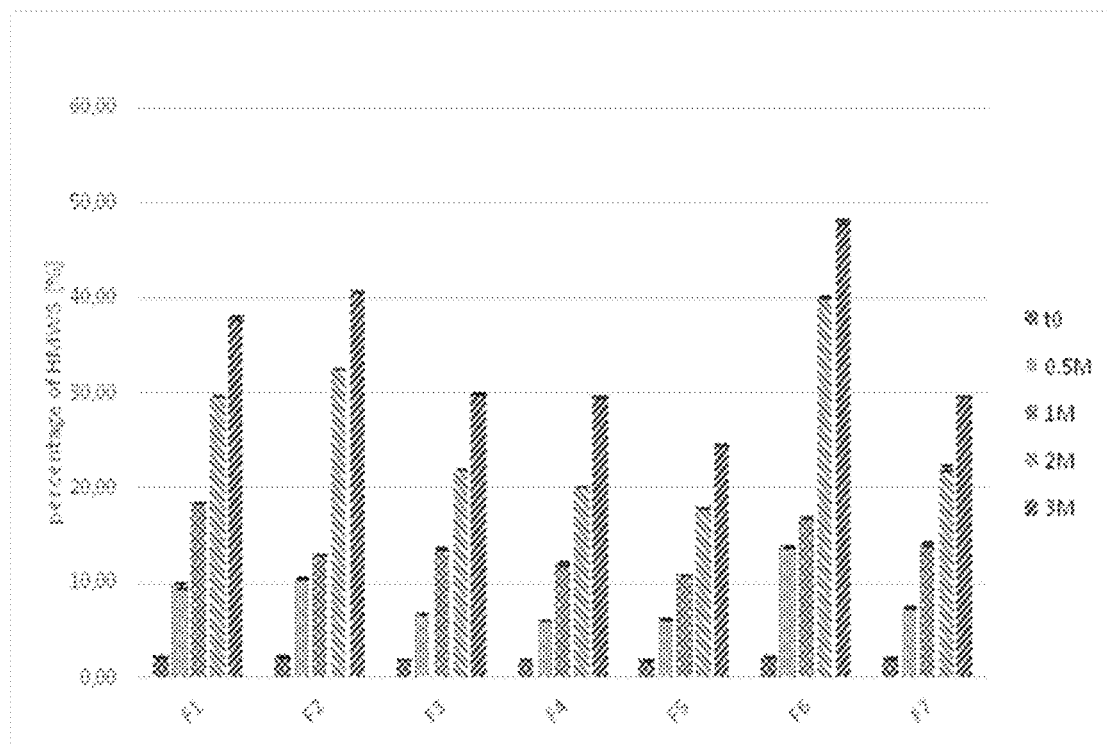
Figure 2:
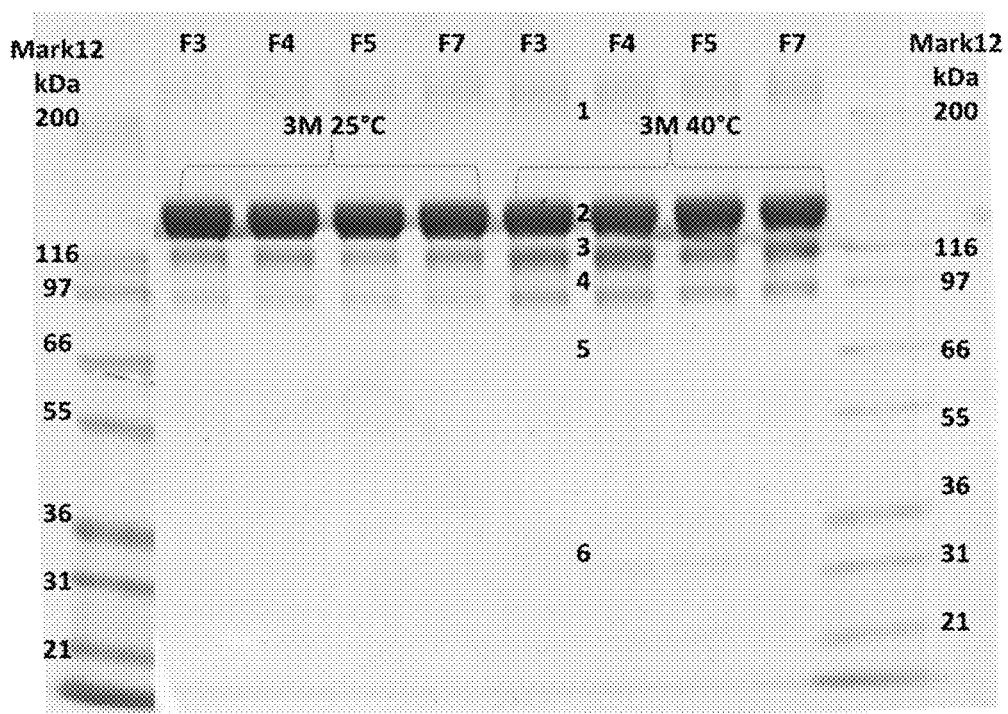

FIG. 2: Analysis of protein fragmentation in samples F3, F4, F5 and F7 after storage for three months at 25° C./60% relative humidity or 40° C./75% relative humidity by SDS-PAGE FIG. 3: Non-reduced SDS-PAGE of the samples S6 and S2 incubated for three months at 40° C./75% relative humidity.

Figure 4:
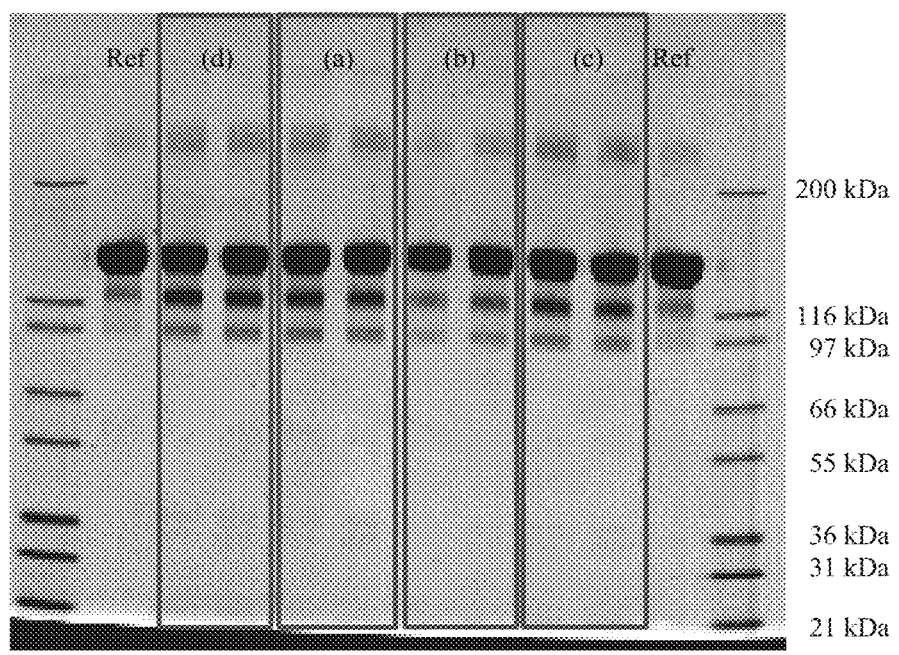

FIG. 4: Non-reduced SDS-PAGE of the samples (a) to (d) shown in Table 9 after three months incubation at 40° C./75% relative humidity.

Figure 5:
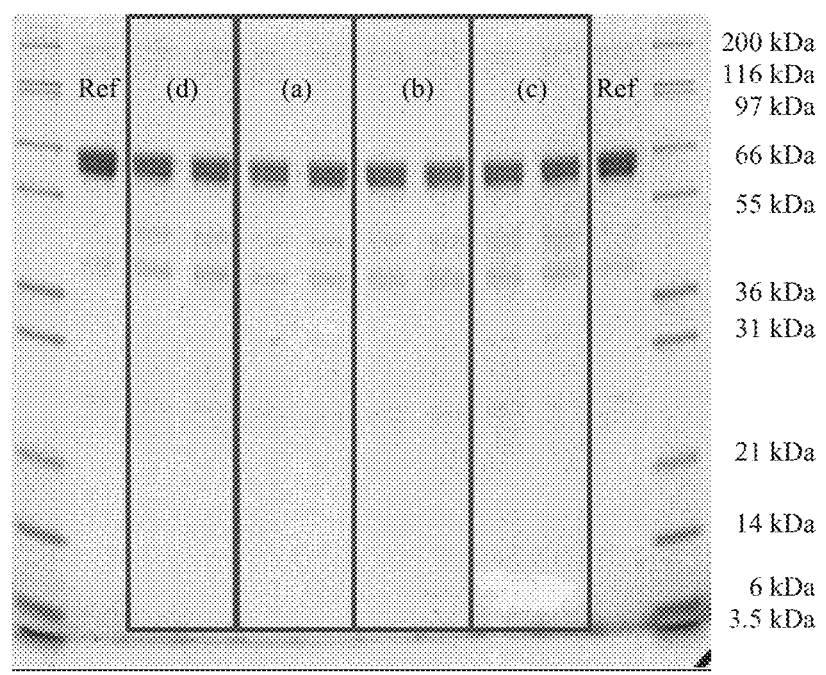

FIG. 5: Reduced SDS-PAGE of the samples (a) to (d) shown in table 9 after three months incubation at 40° C./75% relative humidity.

DETAILED DESCRIPTION OF THE INVENTION

The present invention as illustratively described in the following may suitably be practiced in the absence of any element or elements, limitation or limitations, not specifically disclosed herein.

The present invention will be described with respect to particular embodiments, but the invention is not limited thereto, but only by the claims.

Where the term "comprising" is used in the present description and claims, it does not exclude other elements. For the purposes of the present invention, the term "consisting of" is considered to be a preferred embodiment of the term "comprising". If hereinafter a group is defined to comprise at least a certain number of embodiments, this is also to be understood to disclose a group which preferably consists only of these embodiments.

For the purposes of the present invention, the term "obtained" is considered to be a preferred embodiment of the term "obtainable". If hereinafter e.g. a cell or organism is defined to be obtainable by a specific method, this is also to be understood to disclose a cell or organism which is obtained by this method.

Where an indefinite or definite article is used when referring to a singular noun, e.g. "a", "an" or "the", this includes a plural of that noun unless something else is specifically stated.

The term "pharmaceutical composition" as used herein refers to any composition comprising a chemical substance or active ingredient which composition is intended for use in the medical cure, treatment, or prevention of disease and which is in such a form as to permit the active ingredient to be effective. In particular, a pharmaceutical composition does not contain excipients which are unacceptably toxic to a subject to which the composition is to be administered. The pharmaceutical compositions are sterile, i.e. aseptic and free from all living microorganisms and their spores. The pharmaceutical composition used in the present invention is liquid and stable.

In a "liquid composition" the pharmaceutically active agent, e.g. the VEGF antagonist, can be combined with a variety of excipients to ensure a stable active medication following storage. The liquid pharmaceutical composition used in the invention is at no point lyophilised, i.e. the production method does not contain a lyophilisation step and the composition is not lyophilised for storage. Liquid compositions can be stored in vials, IV bags, ampoules, cartridges, and prefilled or ready-to-use syringes.

A "stable" liquid composition is one in which the VEGF antagonist contained therein essentially retains its physical stability and/or chemical stability and/or biological activity upon storage for a certain period. Preferably, the composition essentially retains upon storage its physical and chemical stability, as well as its biological activity. Various analytical techniques for measuring protein stability are available in the art and are reviewed, for example, in Peptide and Protein Drug Delivery, 247-301, Vincent Lee Ed, Marcel Dekker, Inc, New York, N.Y., Pubs (1991) and Jones, Adv Drug Delivery Rev, 1993, 10:29-90. For example, stability can be measured at a selected temperature for a selected time period. Stability can be evaluated qualitatively and/or quantitatively in a variety of different ways, including evaluation of aggregate formation (for example using size exclusion chromatography, by measuring turbidity, and/or by visual inspection), by assessing charge heterogeneity using cation exchange chromatography or capillary zone electrophoresis, amino-terminal or carboxy-terminal sequence analysis, mass spectrometric analysis, SDS-PAGE analysis to detect aggregated or fragmented molecules, peptide map (for example tryptic or LYS-C) analysis, evaluating biological activity or binding of the antagonist, etc.

Preferably, the pharmaceutical composition is stable at a temperature of about 40° C. for at least 1 to 2 weeks, and/or is stable at a temperature of about 5° C. for at least 3 months, and/or is stable at a temperature of about 25° C. for at least two weeks or one month. Furthermore, the formulation is preferably stable following freezing (to, e.g., −20° C.) and thawing of the formulation at 25° C. as described in the examples herein, for example following 1, 2, 3 or 4 cycles of freezing and thawing.

For example, in the pharmaceutical composition used in the present invention the percentage of high molecular weight species relative to the total amount of the VEGF antagonist as measured by size exclusion chromatography is not more than 4%, preferably not more than 3.5% or 3.25%, more preferably not more than 3.0% or 2.75% and most preferably not more than 2.5% after storage of the composition at 5° C. for 3 months.

A "buffer" is an aqueous solution consisting of a mixture of a weak acid and its conjugate base or vice versa which resists changes in its pH and therefore keeps the pH at a nearly constant value. The buffer of the present invention preferably has a pH in the range from about 6.0 to about 7.0, preferably from about 6.1 to about 6.8, more preferably from about 6.0 to 6.5, even more preferably from about 6.2 to 6.5 and most preferably has a pH of about 6.2 or 6.5.

The buffer used in the present invention is a histidine-containing buffer. Preferably, the histidine-containing buffer is the only buffer present in the liquid formulation of the present invention.

The terms "histidine-containing buffer" and "histidine buffer" are used interchangeably herein and refer to a buffer comprising histidine. Examples of histidine buffers include histidine chloride, histidine hydrochloride, histidine acetate, histidine phosphate, and histidine sulphate. The preferred histidine buffer of the invention further comprises L-histidine. Even more preferably the histidine buffer of the invention comprises histidine hydrochloride, most preferably it comprises histidine hydrochloride and L-histidine. Preferably, the histidine buffer or histidine hydrochloride buffer or histidine hydrochloride/L-histidine buffer has a pH in the range from about 6.0 to about 7.0, preferably from about 6.1 to about 6.8, more preferably from about 6.0 to 6.5, even more preferably from about 6.2 to 6.5 and most preferably has a pH of about 6.2 or 6.5.

In a particular preferred embodiment, the histidine-containing buffer comprises histidine hydrochloride/L-histidine in a concentration in the range of 1 mM to 40 mM, preferably of 2 mM to 35 mM, more preferably of 3 mM to 30 mM, even more preferably of 5 mM to 20 mM and most preferably of 8 mM to 15 mM.

In another particular preferred embodiment the buffer is histidine hydrochloride/L-histidine with a concentration of 10 mM.

In another particular preferred embodiment the buffer is histidine hydrochloride/L-histidine with a concentration of 10 mM and with a pH of 6.2 or 6.5.

The pharmaceutical compositions of the present invention are preferably prepared by dissolving L-histidine, L-histidine-HCl, the carbohydrate, preferably sucrose, and the inorganic salt, preferably sodium chloride, in water before adding the non-ionic surfactant, preferably polysorbate 20 and then adding the VEGF antagonist.

A "surfactant" as used herein refers to an amphiphilic compound, i.e. a compound containing both hydrophobic groups and hydrophilic groups which lowers the surface tension (or interfacial tension) between two liquids or between a liquid and a solid. A "non-ionic surfactant" has no charged groups in its head. The formation of insoluble particles during freeze/thaw cycles of antibody-containing compositions can be remarkably inhibited by addition of surfactants. Examples of "non-ionic surfactants" include e.g. polyoxyethylene glycol alkyl ethers, such as octaethylene glycol monododecyl ether, pentaethylene glycol monododecyl ether; polyoxypropylene glycol alkyl ethers; glucoside alkyl ethers, such as decyl glucoside, lauryl glucoside, octyl glucoside; polyoxyethylene glycol octylphenol ethers, such as triton X-100; polyoxyethylene glycol alkylphenol ethers, such as nonoxynol-9; glycerol alkyl esters, such as glyceryl laurate; polyoxyethylene glycol sorbitan alkyl esters, such as polysorbate; sorbitan alkyl esters, such as spans; cocamide MEA, cocamide DEA, dodecyldimethylamine oxide; block copolymers of polyethylene glycol and polypropylene glycol, such as poloxamers; and polyethoxylated tallow amine (POEA). The pharmaceutical compositions of the present invention can contain one or more of these surfactants in combination.

Preferred non-ionic surfactants for use in the pharmaceutical compositions of the present invention are polysorbates such as polysorbate 20, 40, 60 or 80, and especially polysorbate 20 (i.e. Tween 20).

The concentration of the non-ionic surfactant is in the range of 0.01 to 0.08% (w/v), preferably in the range of 0.015 to 0.06% (w/v), more preferably in the range of 0.02 to 0.04% (w/v) and most preferably it is 0.03% (w/v), relative to the total volume of the composition.

In a preferred embodiment, the non-ionic surfactant is polysorbate 20 with a concentration in the range of 0.015 to 0.06% (w/v), more preferably in the range of 0.02 to 0.04% (w/v) and most preferably it is 0.03% (w/v), relative to the total volume of the composition.

In a particularly preferred embodiment the non-ionic surfactant is polysorbate 20 with a concentration of 0.03% (w/v), relative to the total volume of the composition.

Herein, an "inorganic salt" refers to a ionic compound which has osmoregulatory properties. An inorganic salt such as sodium chloride (NaCl) can dissociate in solution into its constituent ions, i.e. NaCl dissociates into $Na^+$ and $Cl^-$ ions, which both affect the osmotic pressure, i.e. the osmolality, of the solution. Preferred inorganic salts for use in the pharmaceutical formulation of the present invention are potassium chloride, calcium chloride, sodium chloride, sodium phosphate, potassium phosphate and sodium bicarbonate. Preferably the inorganic salt is a sodium salt, more preferably it is sodium chloride (NaCl).

The concentration of the inorganic salt in the pharmaceutical composition used in the present invention is preferably in the range of 20 to 100 mM, more preferably in the range of 25 to 80 mM, even more preferably the inorganic salt has a concentration in the range of 30 to 60 mM or 35 to 45 mM, and most preferably the concentration is 40 mM.

In a particular preferred embodiment, the inorganic salt is NaCl with a concentration in the range of 20 to 100 mM, more preferably in the range of 25 to 80 mM, even more preferably the inorganic salt has a concentration in the range of 30 to 60 mM or 35 to 45 mM, and most preferably the concentration is 40 mM.

In a most preferred embodiment the inorganic salt is NaCl with a concentration of 40 mM.

In a further embodiment the pharmaceutical composition comprises an inorganic salt, preferably NaCl, preferably in a concentration of 40 mM, polysorbate 20 in a concentration of 0.03% (w/v), sucrose in a concentration of 5% (w/v) and a histidine hydrochloride/L-histidine buffer with a concentration of 10 mM and a pH of 6.5, or a histidine hydrochloride/L-histidine buffer with concentration of 10 mM and a pH of 6.2.

The term "VEGF antagonist" refers to a molecule which specifically interacts with VEGF and inhibits one or more of its biological activities, e.g. its mitogenic, angiogenic and/or vascular permeability activity. It is intended to include both anti-VEGF antibodies and antigen-binding fragments thereof and non-antibody VEGF antagonists.

Non-antibody VEGF antagonists include aflibercept, pegaptanib and antibody mimetics. Preferably, the non-antibody VEGF antagonist is aflibercept. Aflibercept which is presently marketed under the name Eylea® and which is also known as VEGF-trap is a recombinant human soluble VEGF receptor fusion protein in which the second immunoglobulin-like domain of VEGF receptor 1 and the third immunoglobulin-like domain of VEGF receptor 2 are fused to the Fc portion of human IgG1 (Holash et al. (2002) Proc. Natl. Acad. Sci. USA 99(17): 11393-11398; WO 00/75319 A1). The CAS number of aflibercept is 862111-32-8. It has received a marketing authorization for the treatment of wet age-related macular degeneration, visual impairment due to diabetic macular oedema (DME) and diabetic retinopathy in patients with diabetic macular edema. The present commercial aflibercept formulation contains sodium phosphate, sodium chloride, polysorbate 20, sucrose and water for injection and is supplied in a concentration of 40 mg/ml.

Pegaptanib which is presently marketed under the name Macugen® is a pegylated anti-vascular endothelial growth factor (VEGF) aptamer (Bell et al. (1999) In Vitro Cell Dev Biol Anim 35(9): 533-42). Antibody mimetics which are VEGF antagonists include binding proteins comprising an ankyrin repeat domain that binds VEGF and inhibits its binding to the receptor, such as DARPin® MP0112 (see also WO 2010/060748 and WO 2011/135067).

The term "antibody" or "immunoglobulin" is used herein in the broadest sense and includes full length antibodies, genetically engineered antibodies, recombinant antibodies, multivalent antibodies, monoclonal antibodies, polyclonal antibodies, bispecific antibodies, multispecific antibodies, chimeric antibodies, humanized antibodies, fully human antibodies, as well as fragments of such antibodies as long as they remain functional and exhibit the desired biological activity. The "Biological activity" of an antibody refers to the ability of the antibody to bind to antigen and result in a biological response which can be measured in vitro or in vivo.

A full length antibody comprises an antigen-binding variable region of the light ($V_L$) and heavy chain ($V_H$), a light chain constant region ($C_L$) and heavy chain constant domains $C_H1$, $C_H2$ and $C_H3$.

The term "antibody fragment" or "antigen-binding fragment" is used herein in the broadest sense and comprises a portion of a full length antibody, preferably comprising the antigen-binding or variable region thereof An antibody fragment retains the original specificity of the parent immunoglobulin. Examples of antibody fragments include, e.g., Fab, Fab', $F(ab')_2$, and Fv fragments, diabodies, linear antibodies, single-chain antibody molecules, and multispecific antibodies formed from antibody fragment(s). Preferably, the antibody fragment is a Fab fragment.

A "monoclonal antibody" is an antibody that is specific for a single epitope of an antigen, i.e. directed against a single determinant on an antigen. Methods for producing monoclonal antibodies are known to the person skilled in the art.

The term "recombinant antibody" refers to all antibodies prepared, expressed, created or isolated by recombinant means, such as antibodies isolated from a transgenic host cell, such as e.g. a NS0 or CHO cell, or from an animal transgenic for immunoglobulin genes, or antibodies expressed using recombinant expression vectors transfected into a host cell, such as e.g. SP 2/0 mouse myeloma cells.

A "humanised antibody" is a human antibody wherein the antigen binding portion (CDR) is derived from non-human species, such as a mouse, and thus has a different specificity compared to the parent immunoglobulin. The CDR protein sequences can be modified to increase their similarities to antibody variants produced naturally in humans.

The term "anti-VEGF antibody" refers to an antibody or antibody fragment such as a Fab or a scFV fragment that specifically binds to VEGF and inhibits one or more of its biological activities, e.g. its mitogenic, angiogenic and/or vascular permeability activity. Anti-VEGF antibodies act, e.g., by interfering with the binding of VEGF to a cellular receptor, by interfering with vascular endothelial cell activation after VEGF binding to a cellular receptor, or by killing cells activated by VEGF. Anti-VEGF antibodies include, e.g., antibodies A4.6.1, bevacizumab, ranibizumab, G6, B20, 2C3, and others as described in, for example, WO 98/45331, US 2003/0190317, U.S. Pat. Nos. 6,582,959, and 6,703,020, WO 98/45332, WO 96/30046, WO 94/10202, WO 2005/044853, EP 0 666 868 B1, WO 2009/155724 and Popkov et al. (2004) J. Immunol. Meth. 288: 149-64. Preferably, the anti-VEGF antibody or antigen-binding fragment thereof present in the pharmaceutical composition used in the present invention is ranibizumab or bevacizumab. Most preferably, it is ranibizumab or an antigen-binding fragment thereof.

"Ranibizumab" is a humanised monoclonal Fab fragment directed against VEGF-A having the light and heavy chain variable domain sequences of Y0317 as described in SEQ ID Nos. 115 and 116 of WO 98/45331 and Chen et al. (1999) J. Mol. Biol. 293: 865-81. The CAS number of ranibizumab is 347396-82-1. Ranibizumab inhibits endothelial cell proliferation and neovascularisation and has been approved for the treatment of neovascular (wet) age-related macular degeneration (AMD), the treatment of visual impairment due to diabetic macular oedema (DME), the treatment of visual impairment due to macular oedema secondary to retinal vein occlusion (branch RVO or central RVO), or treatment of visual impairment due to choroidal neovascularisation (CNV) secondary to pathologic myopia. Ranibizumab is related to bevacizumab and derived from the same parent mouse antibody as bevacizumab but it is much smaller than the parent molecule and has been affinity matured to provide stronger binding to VEGF-A. Ranibizumab is produced recombinantly in *Escherichia coli*, e.g. as described in WO 98/45331 A2. The present commercial ranibizumab formulation contains α,α-trehalose dihydrate, histidine hydrochloride monohydrate, histidine, polysorbate 20 and water for injection and is supplied in a concentration of 10 mg/ml.

"Bevacizumab" is a full-length, humanized murine monoclonal antibody that recognizes all isoforms of VEGF and which is the parent antibody of ranibizumab. The CAS number of bevacizumab is 216974-75-3. Bevacizumab inhibits angiogenesis and is presently approved for the treatment of different cancer types. However, it is also used off-label in ophthalmological diseases such as age-related macular degeneration. The present commercial bevacizumab formulation contains α,α-trehalose dihydrate, sodium phosphate, polysorbate 20 and water for injection and is supplied as a concentrate with a concentration of 25 mg/ml.

In one embodiment, the VEGF antagonist is the only pharmacologically active agent within the formulation. In an alternative embodiment, the formulation contains one or more pharmacologically active agents in addition to the VEGF antagonist. A pharmacologically active agent is able to exert a pharmacological effect when administered to a subject. Preferably, the additional pharmacologically active agent is a PDGF antagonist or an Ang2 antagonist. More preferably, the PDGF antagonist is an anti-PDGF antibody such as rinucumab or an aptamer such as E10030, marketed as Fovista®. Most preferably, the PDGF antagonist is E10030 which is described in Green et al. (1996) Biochemistry 35: 14413; U.S. Pat. Nos. 6,207,816; 5,731,144; 5,731,424; and 6,124,449. Also more preferably, the Ang2 antibody is an anti-Ang2 antibody and most preferably it is nesvacumab.

The concentration of the VEGF antagonist in the pharmaceutical compositions is typically 5-80 mg/ml, preferably 7-60 mg/ml, more preferably 8-50 mg/ml and most preferably 10 or 40 mg/ml. If the VEGF antagonist is aflibercept, the concentration of the VEGF antagonist, i.e. aflibercept, is preferably 40 mg/ml. If the VEGF antagonist is ranibizumab, the concentration of the VEGF antagonist, i.e. ranibizumab, is preferably 6 or 10 mg/ml.

The term "carbohydrate" refers to an organic compound comprising only carbon, hydrogen, and oxygen, usually with a hydrogen:oxygen atom ratio of 2:1 and the empirical formula $Cm(H_2O)_n$. The term "carbohydrate" includes mono-, di-, oligo- and polysaccharides. Examples of carbohydrates include glucose, fructose, galactose, xylose, ribose, sucrose, mannose, lactose, maltose, trehalose, starch, and glycogen. Various other forms of sugars are known, e.g., sugar alcohols such as glycerol, mannitol, sorbitol, and xylitol; sugar acids, e.g. aldonic acids such as ascorbic acid, aldaric acids such as tartaric acid; reducing sugars, e.g. glucose, glyceraldehydes, galactose, lactose, and maltose; amino sugars, e.g. N-acetylglucosamine, galactosamine, glucosamine, and sialic acid; or sulfoquinovose, a sulphonic acid derivative of glucose.

The pharmaceutical composition used in the present invention may further contain diluents, solubilising agents, isotonising agents, excipients, pH-modifiers, soothing agents, buffers, sulphur-containing reducing agents, antioxidants or the like. The pharmaceutical composition used in the present invention does not contain PEG3350 and/or glycine.

Preferably, the pharmaceutical composition used in the present invention contains histidine hydrochloride/L-histidine, polysorbate 20, NaCl, sucrose, water and aflibercept and no further components or active substances, i.e. the pharmaceutical composition consists of histidine hydrochloride/L-histidine, polysorbate 20, NaCl, sucrose, water and aflibercept. More preferably, the pharmaceutical composition used in the present invention consists of 10 mM histidine hydrochloride/L-histidine, 0.03% (w/v) polysorbate 20, 40 mM NaCl, 5% (w/v) sucrose, water and 40 mg/ml aflibercept.

Also preferably, the pharmaceutical composition used in the present invention contains histidine hydrochloride/L-histidine, polysorbate 20, NaCl, sucrose, water and ranibizumab and no further components or active substances, i.e. the pharmaceutical composition consists of histidine hydrochloride/L-histidine, polysorbate 20, NaCl, sucrose, water and ranibizumab. More preferably, the pharmaceutical composition used in the present invention consists of 10 mM histidine hydrochloride/L-histidine, 0.03% (w/v) polysorbate 20, 40 mM NaCl, 5% (w/v) sucrose, water and 10 mg/ml ranibizumab.

An "intraocular neovascular disease" is a disease characterized by ocular neovascularisation. Examples of intraocular neovascular diseases include, e.g., proliferative retinopathies, choroidal neovascularisation (CNV), age-related macular degeneration (AMD), diabetic and other ischemia-related retinopathies, diabetic macular oedema, pathological myopia, von Hippel-Lindau disease, histoplasmosis of the eye, Central Retinal Vein Occlusion (CRVO), Branch Retinal Vein Occlusion (BRVO), corneal neovascularisation, and retinal neovascularisation. The term "age-related macular degeneration" refers to a medical condition which usually affects older adults and results in a loss of vision in the centre of the visual field (the macula) because of damage to the retina.

If the VEGF antagonist present in the pharmaceutical composition used in the present invention is aflibercept, the pharmaceutical composition is preferably for use in the treatment of neovascular (wet) age-related macular degeneration (AMD), visual impairment due to macular oedema secondary to retinal vein occlusion (branch RVO or central RVO), visual impairment due to diabetic macular oedema (DME) or visual impairment due to myopic choroidal neovascularisation (myopic CNV).

If the VEGF antagonist present in the pharmaceutical composition used in the present invention is ranibizumab, the pharmaceutical composition is preferably for use in the treatment of neovascular (wet) age-related macular degeneration (AMD), of visual impairment due to diabetic macular edema (DME), of visual impairment due to macular edema secondary to retinal vein occlusion (branch RVO or central RVO) or of visual impairment due to choroidal neovascularisation (CNV) secondary to pathologic myopia (PM).

The term "intravitreal injection" refers to the administration of a pharmaceutical composition in which the substance is injected directly into the eye. More specifically, the substance is injected into the vitreous humour (also called vitreous body or simply vitreous) which is the clear gel that fills the space between the lens and the retina of the eyeball of humans and other vertebrates.

Pharmaceutical compositions of the present invention can be supplied in sealed and sterilized plastic, glass or other suitable containers having a defined volume such as vials, ampoules or syringes or a large volume such as bottles.

It is preferred that the liquid pharmaceutical composition containing a VEGF antagonist, preferably aflibercept or ranibizumab, is supplied in a prefilled syringe. A "ready-to-use syringe" or "prefilled syringe" is a syringe which is supplied in a filled state, i.e. the pharmaceutical composition to be administered is already present in the syringe and ready for administration. Prefilled syringes have many benefits compared to separately provided syringe and vial, such as improved convenience, affordability, accuracy, sterility, and safety. The use of prefilled syringes results in greater dose precision, in a reduction of the potential for needle sticks injuries that can occur while drawing medication from vials, in pre-measured dosage reducing dosing errors due to the need to reconstituting and/or drawing medication into a syringe, and in less overfilling of the syringe helping to reduce costs by minimising drug waste. The barrel of the pre-filled syringe may be made of glass or plastic. Preferably, the barrel of the pre-filled syringe is made of plastic, more preferably of cyclic olefin polymer. Preferably, the barrel of the pre-filled syringe is not coated with silicone.

In a preferred embodiment the pH of the liquid pharmaceutical composition used in the present invention is in the range from about 6.0 to about 7.0, preferably from about 6.1 to about 6.8, more preferably from about 6.0 to 6.5, even more preferably from about 6.2 to 6.5 and most preferably has a pH of about 6.2 or 6.5.

The liquid pharmaceutical composition used in the present invention is to be used in the treatment of an intraocular neovascular disease such as age-related macular degeneration (AMD), in the treatment of visual impairment due to diabetic macular oedema (DME), in the treatment of visual impairment due to macular oedema secondary to retinal vein occlusion (branch RVO or central RVO), or in the treatment of visual impairment due to choroidal neovascularisation (CNV) secondary to pathologic myopia.

In particular, the invention relates to a liquid pharmaceutical composition for use in the treatment of an intraocular neovascular disease such as AMD comprising a histidine-containing buffer, a non-ionic surfactant, an inorganic salt, a carbohydrate and a VEGF antagonist.

In one embodiment of the invention the liquid pharmaceutical composition for intravitreal administration for use in the treatment of an intraocular neovascular disease such as AMD comprises a histidine-containing buffer, a non-ionic surfactant, an inorganic salt, a carbohydrate and a VEGF antagonist.

In a preferred embodiment of the invention the liquid pharmaceutical composition for intravitreal administration for use in the treatment of an intraocular neovascular disease such as AMD comprises a histidine-containing buffer in a concentration of 1mM to 40 mM, a non-ionic surfactant in a concentration of 0.01 to 0.08% (w/v), an inorganic salt in a concentration of 20 to 100 mM, a carbohydrate in a concentration of 3 to 20% (w/v) and a VEGF antagonist.

In another preferred embodiment of the invention the liquid pharmaceutical composition for intravitreal administration for use in the treatment of an intraocular neovascular disease such as AMD comprises histidine hydrochloride/L-histidine in a concentration of 1 mM to 40 mM, polysorbate 20 in a concentration of 0.01 to 0.08% (w/v), NaCl in a concentration of 20 to 100 mM, sucrose in a concentration of 3 to 20% (w/v) and aflibercept.

In another preferred embodiment of the invention the liquid pharmaceutical composition for intravitreal administration for use in the treatment of an intraocular neovascular disease such as AMD comprises 10 mM histidine hydrochloride/L-histidine, 0.03% (w/v) polysorbate 20, 40 mM NaCl, 5% (w/v) sucrose and aflibercept.

In another preferred embodiment of the invention the liquid pharmaceutical composition for intravitreal administration for use in the treatment of an intraocular neovascular disease comprises 10 mM histidine hydrochloride/L-histidine, 0.03% (w/v) polysorbate 20, 40 mM NaCl, 5% (w/v) sucrose and 40 mg/ml aflibercept.

In another preferred embodiment of the invention the liquid pharmaceutical composition for intravitreal administration for use in the treatment of an intraocular neovascular disease consists of 10 mM histidine hydrochloride/L-histidine, 0.03% (w/v) polysorbate 20, 40 mM NaCl, 5% (w/v) sucrose and 40 mg/ml aflibercept.

In another preferred embodiment of the invention the liquid pharmaceutical composition for intravitreal administration for use in the treatment of an intraocular neovascular disease consists of 10 mM histidine hydrochloride/L-histidine, 0.03% (w/v) polysorbate 20, 40 mM NaCl, 5% (w/v) sucrose and 40 mg/ml aflibercept and has a pH of 6.2 or 6.5.

In another preferred embodiment of the invention the liquid pharmaceutical composition for intravitreal administration for use in the treatment of an intraocular neovascular disease such as AMD comprises histidine hydrochloride/L-histidine in a concentration of 1 mM to 40 mM, polysorbate 20 in a concentration of 0.01 to 0.08% (w/v), NaCl in a concentration of 20 to 100 mM, sucrose in a concentration of 3 to 20% (w/v) and ranibizumab.

In another preferred embodiment of the invention the liquid pharmaceutical composition for intravitreal administration for use in the treatment of an intraocular neovascular disease such as AMD comprises 10 mM histidine hydrochloride/L-histidine, 0.03% (w/v) polysorbate 20, 40 mM NaCl, 5% (w/v) sucrose and ranibizumab.

In another preferred embodiment of the invention the liquid pharmaceutical composition for intravitreal administration for use in the treatment of an intraocular neovascular disease comprises 10 mM histidine hydrochloride/L-histidine, 0.03% (w/v) polysorbate 20, 40 mM NaCl, 5% (w/v) sucrose and 6 or 10 mg/ml ranibizumab.

In another preferred embodiment of the invention the liquid pharmaceutical composition for intravitreal administration for use in the treatment of an intraocular neovascular disease consists of 10 mM histidine hydrochloride/L-histidine, 0.03% (w/v) polysorbate 20, 40 mM NaCl, 5% (w/v) sucrose and 6 or 10 mg/ml ranibizumab.

In another preferred embodiment of the invention the liquid pharmaceutical composition for intravitreal administration for use in the treatment of an intraocular neovascular disease consists of 10 mM histidine hydrochloride/L-histidine, 0.03% (w/v) polysorbate 20, 40 mM NaCl, 5% (w/v) sucrose and 6 or 10 mg/ml ranibizumab and has a pH of 6.2 or 6.5.

Moreover, the invention encompasses the intravitreal administration of the liquid pharmaceutical composition of the invention to a subject in an effective amount to treat an intraocular neovascular disease such as AMD. In a preferred embodiment, the liquid pharmaceutical composition of the invention for intravitreal administration is present in a prefilled syringe.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

The detailed description is merely exemplary in nature and is not intended to limit application and uses. The following examples further illustrate the present invention without, however, limiting the scope of the invention thereto. Various changes and modifications can be made by those skilled in the art on the basis of the description of the invention, and such changes and modifications are also included in the present invention.

EXAMPLES

Examples 1.1 to 1.4 relate to a first set of stability tests performed with the seven compositions of Table 1 below. Examples 2.1 to 2.6 show the result of stability tests of samples 2 and 6 as described in Table 2 in prefilled syringes. Examples 3.1 to 3.9 relate to a second set of stability tests performed with the four compositions of Table 9.

Example 1

First Set of Stability Tests

Example 1.1

Preparation of Samples

Different formulations of aflibercept were prepared according to Table 1.

TABLE 1

Pharmaceutical compositions tested. Sample 7 corresponds to the commercially available aflibercept (Eylea ®) formulation.

| | buffer | inorganic salt | surfactant | carbohydrate |
|---|---|---|---|---|
| 1 | 10 mM sodium citrate, pH 6.2 | 40 mM NaCl | 0.03% PS 20 | 5% sucrose |
| 2 | 10 mM sodium citrate, pH 6.2 | — | 0.03% PS 20 | 10% sucrose |
| 3 | 10 mM L-His/HisHCl; pH 6.2 | 40 mM NaCl | 0.03% PS 20 | 5% sucrose |
| 4 | 10 mM L-His/HisHCl; pH 6.2 | — | 0.03% PS 20 | 10% sucrose |
| 5 | 10 mM L-His/HisHCl; pH 6.5 | 40 mM NaCl | 0.03% PS 20 | 5% sucrose |
| 6 | 10 mM L-His/HisHCl; pH 6.2 | 150 mM NaCl | 0.01% PS 20 | — |
| 7 | 10 mM sodium phosphate; pH 6.2 | 40 mM NaCl | 0.03% PS 20 | 5% sucrose |

All pharmaceutical compositions listed above contained 40 mg/ml of aflibercept.

The pharmaceutical compositions were prepared without aflibercept, which was dialyzed into them afterwards. The excipients sucrose, potentially sodium chloride and the surfactant polysorbate 20 were dissolved in the indicated concentrations of the buffering components L-histidine and L-histidine hydrochloride or tri-sodium citrate and citric acid, respectively. The ratio of basic and acidic components of the buffer led to a pH of 6.2 or 6.5, respectively. The osmolality was determined by Gonotec Osmomat 030. All formulations were adjusted to 300mOsmol/kg +/−20 mOsm/kg to reach isotonicity.

Before dialysis the dialysis tubes were hydrated with $H_2O$. Dialysis of pooled aflibercept was conducted overnight at 6° C. by regenerated cellulose membranes with a molecular weight cut off 12 kDa-14 kDa. After dialysis the concentration of aflibercept was adjusted to 40 mg/mL +/−2 mg/mL by centrifugal filters Vivaspin 6, MWCO 50 kDa and the aflibercept formulations were sterile filtered (0.2 μm PVDF membrane syringe filters) and aseptically filled into pre-sterilized 2 mL FIOLAX type I glass vials.

Example 1.2

Test Conditions

To identify the most stable formulation the samples were analyzed after subjecting them to different conditions.

In one set of experiments, the samples were subjected to different stress conditions. These stress conditions were chosen to force the chemical and physical degradation pathways of aflibercept and included the following conditions:
a) shaking (samples were shaken with 300 rpm at 25° C. for 7 days), and
b) freeze/thaw (samples were frozen and thawed three times (25° C. to −20° C.) with a rate of ±1° C./min; after each cooling/heating step the temperature (25° C. and −20° C. respectively) was kept constant for 10 minutes).

In another set of experiments, the samples were stored at a temperature of 5° C. for one or three months or at temperatures of 25° C. and 60% relative humidity or 40° C. and 75% relative humidity for two weeks, one, two or three months.

After the samples had been subjected to the different conditions as outlined above, aliquots were taken and subjected to analysis, e.g. by sodium dodecylsulphate polyacrylamide gel electrophoresis (SDS-PAGE) and size exclusion chromatography.

Example 1.3

Analysis by Size Exclusion Chromatography

Size exclusion chromatography was employed to detect high molecular weight species (HMWS), i.e. aggregates of aflibercept.

Size exclusion chromatography (SEC) uses porous particles to separate molecules of different sizes. It is generally used to separate biological molecules according to their molecular mass and shape in diluted solution. The stationary phase consists of spherical porous particles of controlled pore size through which biomolecules diffuse to different extents based on differences in their molecular sizes. Small molecules diffuse freely into the pores and their movement through the column is retarded, whereas large molecules are unable to enter the pores and are therefore eluted earlier. Hence, molecules are separated in order of decreasing molecular mass, with the largest molecules eluting from the column first.

The samples of the stability program were diluted with SEC eluent to a final concentration of 0.5 mg/mL and stored in HPLC vials at 6° C. until SEC measurement.

The conditions for size exclusion chromatography were as follows:
Column: TSKgel G3000SWXL
Flow rate: 1.0 mL/min, isocratic elution
Column temperature: 25° C.
Autosampler temperature: 6° C.
Detection: UV 214 nm/280 nm
Injection volume: 20 µL (c=0.5 mg/mL)
Eluent:0.02 M sodium phosphate with 0.8M NaCl, pH 6.0
Run time: 20 minutes The results of the detection at 214 nm were used for the evaluation. The main peak and all other sample specific peaks with a signal to noise ratio of ≥10 were evaluated. The areas of particular peaks e.g. aggregated species were compared to the sum of all sample specific peaks with S/N≥10 giving the relative ratio.

The results of this analysis are shown in FIG. 1. When stored for three months at 25° C. or 40° C. formulations F3 and F5 comprising 10 mM L-histidine/histidine hydrochloride, 40 mM NaCl, 5% sucrose and 0.03% polysorbate 20 and having a pH of 6.2 and 6.5, respectively, showed the lowest amounts of high molecular weight species, i.e. of aggregated protein. In particular, the amount of high molecular weight species in formulations F3 and F5 was lower than in the commercially available aflibercept (Eylea®) formulation. Hence, these formulations can be considered more stable than the commercially available aflibercept (Eylea®) formulation.

Example 1.4

SDS PAGE

By SDS-PAGE physical modifications like fragmentation and oligomerisation of aflibercept in the different formulations 1-7 of Table 1 were determined.

The SDS-PAGE was performed under reducing conditions. Samples were diluted to 0.4 mg/ml with water and further diluted to 0.2 mg/ml with reducing SDS sample buffer. The samples were incubated at 95° C. for 5 min. The sample wells were washed with running buffer prior to application of the samples (n=2). After the run the gel was washed with water and dyed with Coomassie overnight. After discoloration the gel was scanned and analyzed using QuantityOne Software.

The running conditions were as follows:
voltage: 125 V
current: 35 mA
power: 5W
time: 110 min The results of the SDS PAGE analysis are shown in FIG. 2.

In the SDS-PAGE analysis of all samples incubated for three months at 25° C. or 40° C. bands representing fragments of aflibercept were visible. The lowest amount of fragments was detectable for formulation F5 which contains 10 mM L-histidine/histidine hydrochloride, pH 6.5, 40 mM NaCl, 5% sucrose and 0.03% polysorbate 20.

Example 2

Stability of Aflibercept Formulations in Prefilled Syringes

Example 2.1

Preparation of Pre-filled Syringes Containing the Aflibercept Formulation

165 µl of a solution containing 40 mg/ml of the VEGF antagonist aflibercept and 10 mM histidine buffer, 40 mM sodium chloride, 5% (w/v) sucrose, 0.03% (w/v) polysorbate 20, pH 6.2 was filled into the syringes as listed in Table 2:

TABLE 2

| No. | Syringe size | Syringe barrel | Syringe type | Silicone level [mg] | Stopper coating |
| --- | --- | --- | --- | --- | --- |
| 2 | 1.0 ml | Borosilicate glass | Luer cone | 0.16 (baked-on) | Fluoropolymer (Flurotec) |
| 6 | 1.0 mL | Cycloolefin polymer | Luer cone | No silicone | Fluoropolymer (Flurotec) |

The syringes as listed in Table 2 were incubated at 5° C., 25° C./60% relative humidity and 40° C./75% relative humidity for one month and 3 months.

Afterwards, the samples were analyzed by UV-Vis for protein concentration, by size exclusion chromatography (SEC) and asymmetric flow field-flow fractionation (AF4) for the presence of high molecular weight species (HMWS), by non-reduced sodium dodecyl sulfate polyacrylamide gel electrophoresis (SDS-PAGE) for the presence of fragments and HMWS, by reduced peptide mapping for the presence of methionine oxidation and deamidation. Isoelectric focusing (IEF) was used to analyze samples for chemical modifications which results in charge variants of aflibercept. Also pH was monitored within the whole incubation period.

During the complete stability program in all samples no significant change as well in protein concentration (spectrophotometric quantification at 280 nm; n=3) and pH (n=2) was detected.

Example 2.2

AF4 Analysis of the Aflibercept Formulation Stored in Prefilled Syringes

The asymmetric flow field flow fractionation (AF4) is a technique to identify and quantify higher molecular weight species of aflibercept based on their size. This separation is obtained by the difference in mobility (diffusion coefficient) in the flow field induced by the liquid flow across the channel. In combination with MALS (multi angle light scattering) and UV (280 nm) as concentration-dependent detector, the aflibercept aggregates can be characterized and quantified.

20 µg aflibercept were loaded onto a 15.5 cm separation channel 15.5 cm (short channel) combined with a W490 separation spacer (both Wyatt Technology) and a PLGC 10 kD SC-5 Membrane (Millipore). The protein was eluted using 0.1 M sodium phosphate (pH 6.0) and 0.02% sodium azide according to elution conditions shown in Table 3 representing the cross flow and focus flow during the separation (channel flow: 0.8 mL/min).

Eluted species were detected at a wavelength of 280 nm and displayed on a graph showing the concentration of the eluted species vs. time. The elution profile showed a main peak with the non-aggregated protein and some further peaks of the protein representing higher molecular weight forms of the protein. The corresponding molecular weights were calculated with a MALLS detector.

TABLE 3

| Step | Delta t [min] | Time [min] | Mode | $X_{Start}$ [mL/min] | $X_{End}$ [mL/min] | FF [mL/min] |
|---|---|---|---|---|---|---|
| 1 | 4.0 | 4.0 | Elution | 1.5 | 1.5 | — |
| 2 | 1.0 | 5.0 | Focus | — | — | 2.0 |
| 3 | 2.0 | 7.0 | Focus + Inj. | — | — | 2.0 |
| 4 | 1.0 | 8.0 | Focus | — | — | 2.0 |
| 5 | 32.0 | 40.0 | Elution | 1.5 | 1.5 | — |
| 6 | 10.0 | 50.0 | Elution | 1.5 | 0.2 | — |
| 7 | 10.0 | 60.0 | Elution | 0.2 | 0.2 | — |
| 8 | 10.0 | 70.0 | Elution + Inj. | 0.2 | 0.0 | — |
| 9 | 10.0 | 80.0 | Elution + Inj. | 0.0 | 0.0 | — |

Table 4 shows the percentage of peak areas for the higher molecular weight species in relation to the total peak areas of the eluted species for the syringes of Table 2 incubated for 1 and 3 months at 40° C./75% relative humidity. Each sample was examined in duplicate measurements unless otherwise noted. All other temperatures (5° C. and 25° C./60% relative humidity) showed no significant increase of higher molecular weight species during storage compared to the starting material.

TABLE 4

| Condition | Syringe | HMWS [%] | SD [%] |
|---|---|---|---|
| T0 | S2 | 1.1 | n.a.[*] |
|  | S6 | 1.1 | n.a.[*] |
| 1 M 40° C. | S2 | 10.7 | 0.1 |
|  | S6 | 10.2 | 0.4 |
| 3 M 40° C. | S2 | 26.8 | 0.7 |
|  | S6 | 26.3 | n.a.[*] |

[*] only single measurement

The generation of HMWS determined by AF4-MALS was highly comparable between the two syringes S2 (glass syringe) and S6 (COP) during incubation at 40° C./75 relative humidity in the period up to 3 months. Both the identities of the higher molecular weight species and the temperature dependent kinetics were comparable between the two primary packaging systems.

Example 2.3

SEC Analysis of the Aflibercept Formulation Stored in Prefilled Syringes

The protein samples from the syringes were loaded onto a TSKgel G3000SWXL, (Tosoh, 300×7.8 mm, 5 μm) column to detect high molecular weight species of aflibercept.

The protein was eluted by isocratic elution using 0.02 M sodium phosphate (pH 6.0) and 0.8 M sodium chloride at a flow rate of 1.0 mL/min at 25° C. Eluted species were detected at a wavelength of 214 nm and displayed on a graph showing the concentration of the eluted species vs. time. The elution profile showed a main peak with the non-aggregated protein and some further peaks of the protein representing higher molecular weight forms of the protein. The area of all peaks was determined. Table 5 shows the percentage of peak area for the aggregates in relation to the total peak area of the eluted species for the syringes of Table 2. Each sample was examined in duplicate measurements.

TABLE 5

| Condition | Syringe | HMWS [%] | SD [%] |
|---|---|---|---|
| T0 | S2 | 2.20 | 0.01 |
|  | S6 | 2.19 | 0.02 |
| 1 M 5° C. | S2 | 2.31 | 0.01 |
|  | S6 | 2.26 | 0.01 |
| 3 M 5° C. | S2 | 2.38 | 0.01 |
|  | S6 | 2.36 | 0.02 |
| 2 W 25° C. | S2 | 2.45 | 0.01 |
|  | S6 | 2.45 | 0.00 |
| 1 M 25° C. | S2 | 2.55 | 0.01 |
|  | S6 | 2.53 | 0.01 |
| 3 M 25° C. | S2 | 3.03 | 0.01 |
|  | S6 | 3.01 | 0.00 |
| 0.5 M 40° C. | S2 | 9.80 | 0.02 |
|  | S6 | 9.76 | 0.06 |
| 1 M 40° C. | S2 | 15.58 | 0.01 |
|  | S6 | 15.49 | 0.06 |
| 3 M 40° C. | S2 | 33.71 | 0.01 |
|  | S6 | 33.93 | 0.05 |

The generation of HMWS determined by SEC was highly comparable during all incubation parameters (temperature, storage time) between the two syringes S2 (glass syringe) and S6 (COP). Both the identities of the higher molecular weight species and the temperature dependent kinetics were comparable between the two primary packaging systems.

Example 2.4

Non-reduced SDS-PAGE Analysis of the Aflibercept Formulation Stored in Prefilled Syringes By non-reduced SDS-PAGE physical modifications like fragmentation and oligomerization of aflibercept in the different syringe systems according to Table 2 were determined.

The SDS-PAGE was performed under non-reducing conditions in a 4-12% Tris-Glycine gel. Samples were prediluted to 0.4 mg/ml with water and further diluted to 0.2 mg/ml with SDS sample buffer. The samples were incubated at 95° C. for 5 min.

After the run the gel was rinsed three times with 100 mL deionized water and dyed with Coomassie overnight at room temperature. After discoloration the gel was scanned and analyzed using QuantityOne Software.

Figure 3:
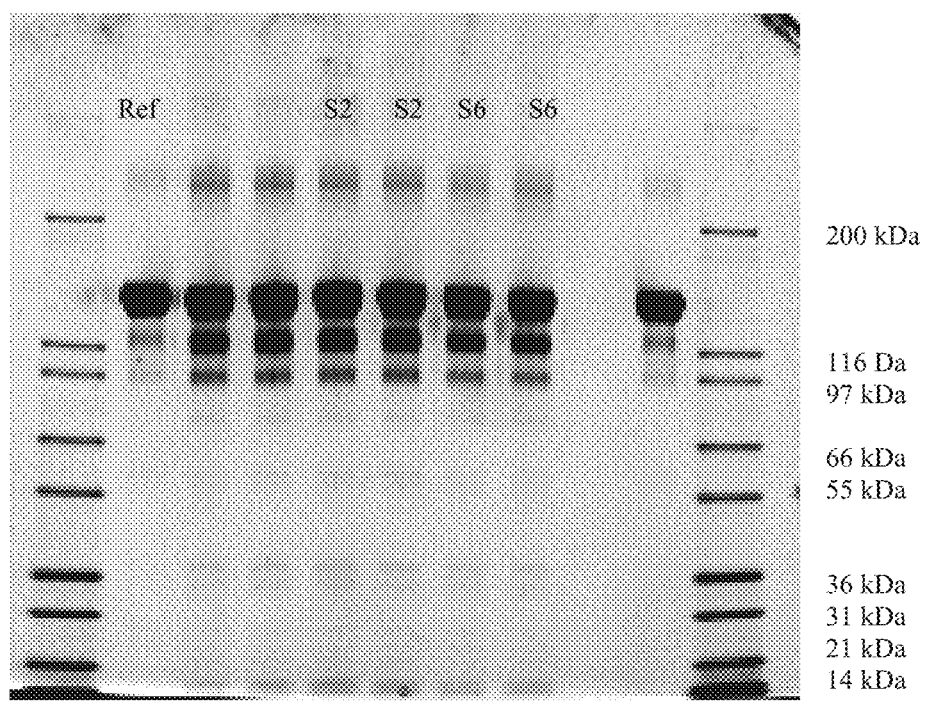

The running conditions were as follows:
voltage: 125 V
current: 35 mA
power: 5W
time: 130 min Non-reduced SDS-PAGE analysis was performed for samples incubated at all temperatures listed above for 3 months. Storing the samples at 5° C. did not lead to significant changes of the banding pattern in all primary packaging systems, no generation of new impurity bands or significant increment of existing impurity bands could be detected in both syringe materials over the whole incubation period. Storing the samples at 25° C./60% relative humidity led to stronger impurity bands, the results of the non-reduced SDS PAGE analysis of 3 months incubated samples at 40° C./75% relative humidity are shown in FIG. 3.

In the non-reduced SDS-PAGE analysis of all samples incubated for three months at 40° C./75 relative humidity bands representing fragments and higher molecular weight species of aflibercept were visible. The generation of fragments and HMWS during the 3 months incubation was highly comparable in the kinetics and the identity of the impurities in both primary packaging systems shown in Table 2.

Example 2.5

IEF Analysis of the Aflibercept Formulation Stored in Prefilled Syringes

Isoelectric focusing (IEF) separates different isoforms of aflibercept due to differences in their isoelectric points because of e.g. deamidation. The ready-to-use IEF gel (Focus Gel (pH 6-11) from Serva, No. 43329.01) contains a pH gradient within the gel. After application, proteins migrate due to their net charge in the pH gradient until they reach the pH equivalent to their isoelectric point (IEP, IP).

Aflibercept samples were diluted to 0.5 mg/ml with ultrapure water. 10 µl thereof equal to 5 µg aflibercept were applied onto the focus gel. Each sample was analyzed as duplicate. After the run the proteins were fixed for 60 minutes in a solution containing 12% (w/v) trichloroacetic acid and 3.5% 5-sulfosalicyl acid dihydrate (w/v), rinsed three times with deionized water and dyed with Coomassie overnight at room temperature. After discoloration with 20% ethanol the gel was scanned with a GS 800 densitometer from BioRad and analyzed. Table 6 shows the focusing conditions:

TABLE 6

| Phase | Time (min) | Power (W) | Current (mA) | Voltage (V) |
|---|---|---|---|---|
| Pre focusing | 20 | 10 | 50 | 1000 |
| Sample entrance | 30 | 10 | 30 | 500 |
| Isoelectric focusing | 90 | 20 | 18 | 1500 |
| Sharpening | 30 | 25 | 15 | 2000 |

In the IEF no change in the banding pattern of aflibercept compared to the reference could be detected in all primary packaging systems after one month storage at all temperatures. After 3 months only samples incubated at 5° C. and 25° C./60% complied with the reference and showed no alteration in comparison to the starting material. Samples incubated at 40° C./75% relative humidity showed a comparable shift to acidic species in all tested primary packaging materials, there was no difference with regard to the different primary packaging materials shown in Table 2.

Example 2.6

Reduced Peptide Mapping Analysis of the Aflibercept Formulation Stored in Prefilled Syringes By reduced peptide mapping the purity of aflibercept with regard to deamidation and methionine oxidation was analyzed after digestion with trypsin and liquid chromatography coupled to mass spectrometry (LC-MS)

After reduction and alkylation, the protein was subjected to enzymatic cleavage with trypsin. The resulting peptides were analyzed by RP-UPLC-MS. During chromatography the peptides were eluted by changing the mobile phase from highly polar (trifluoroacetic acid in water) to less polar (trifluoroacetic acid in acetonitrile) and analyzed by mass spectrometry (Xevo G2-XS QTOF). The peptide data was processed and compared with the theoretical protein sequence and a reference sample to detect oxidations and deamidations.

Syringes shown in Table 2 were analyzed as single measurement after 3 months incubation at 5° C., 25° C./60% relative humidity and 40° C./75 relative humidity and compared to the starting material to.

Samples were diluted with denaturation buffer (50 mM Tris(hydroxymethyl)aminomethane) to a aflibercept concentration of 1.25 mg/mL. 80 µl of the diluted samples were mixed with 10 µl of 0.5% RapiGest (from Waters, solved in 50 mM Tris(hydroxymethyl)amino-methane) and incubated 5 minutes at 95° C. 4.5 µl of 0.02 M DTT (dissolved in 50 mM Tris(hydroxymethyl)-aminomethane) were added for reduction and incubated for 30 minutes at 37° C. For aflibercept digestion 5 µl of a 1 mg/mL Trypsin solution (solved in 50 mM acetic acid) were added and incubated for further 3 hours at 37° C. The reaction was stopped with 20 µl of 2% (v/v) trifluoroacetic acid and an incubation for 30 minutes at 37° C. The supernatant was diluted to 0.125 mg/mL with 50 mM Tris(hydroxymethyl)-aminomethane for analysis of the peptides.

UPLC Parameters:

The digested protein samples from the syringes were loaded onto an ACQUITY UPLC-CSH C-18 column from Waters, 100 mm×2.1 mm, 1.7 µm. 0.25 µg of the digested samples were eluted at 65° C. with a gradient of eluent A (water), eluent B (acetonitrile), eluent C (0.25% trifluoroacetic acid) and D (n-propanol) according to the following Table 7:

TABLE 7

| Time [minutes] | Eluent A [%] | Eluent B [%] | Eluent C [%] | Eluent D [%] |
|---|---|---|---|---|
| 0.0 | 89.0 | 1.0 | 10.0 | 0.0 |
| 2.5 | 89.0 | 1.0 | 10.0 | 0.0 |
| 5.0 | 80.0 | 8.0 | 10.0 | 2.0 |
| 50.0 | 57.5 | 26.0 | 10.0 | 6.5 |
| 52.0 | 0.0 | 72.0 | 10.0 | 18.0 |
| 54.0 | 0.0 | 72.0 | 10.0 | 18.0 |
| 56.0 | 89.0 | 1.0 | 10.0 | 0.0 |
| 60.0 | 89.0 | 1.0 | 10.0 | 0.0 |

Method Parameters for Mass Spectrometry:

| Ionisation type: | ESI | Polarity: | Positive |
|---|---|---|---|
| Analyser mode: | Sensitivity | Experiment type: | MS |
| Start Mass: | 50 m/z | Cone Gas Flow: | 30 L/h |
| End Mass: | 2000 m/z | Desolvation Gas Flow: | 1000 L/h |

-continued

| | | | |
|---|---|---|---|
| Source Temperature: | 120° C. | Scan Time: | 0.5 s |
| Desolvation Temperature: | 450° C. | Capillary Voltage: | 3.0 kV |
| Cone Voltage: | 35 V | | |

LockSpray Profile
Reference Compound: Leucine Enkephalin
MS Lock mass: 556.2766 m/z
Scan Time: 0.5 s
Interval: 30 s 4 oxidated methionine residues in aflibercept could be identified in the peptides (1:T1_AS20, 1:T22, 1:T28, 1:T48) and were summed up for evaluation of the total oxidation (see Table 8). 6 deamidation sites of aflibercept could be identified in the peptides (1:T10_AS12 ; 1 :T11; 1:T10_AS12; 1:T12_AS3; 1:T12_AS3; 1:T30_AS12; 1:T30_AS?; 1:T33_AS14) and were summed up for evaluation of the total deamidation (see Table 8).

TABLE 8

| Condition | Syringe | Total methionine oxidations [%] | Total deamidations [%] |
|---|---|---|---|
| T0 | S2 | 23.1 | 35.3 |
| | S6 | 22.5 | 37.6 |
| 3 M 5° C. | S2 | 27.7 | 36.8 |
| | S6 | 22.4 | 36.9 |
| 3 M 25° C. | S2 | 24.5 | 44.0 |
| | S6 | 23.4 | 45.3 |
| 3 M 40° C. | S2 | 25.7 | 92.0 |
| | S6 | 27.3 | 90.0 |

Both syringes shown in Table 2 comprise an identical stability with regard to methionine oxidation and deamidation. Whereas in all temperature conditions no significant increase of methionine oxidation could be detected in both syringe materials (glass vs. COP), the increase of deamidation was temperature dependent. Both syringe systems comprised a comparable increase of deamidation in the stability program.

From the results shown it is apparent that the stability of an aflibercept formulation of the present invention in a pre-filled plastic syringe (syringe 6) is at least comparable with the stability in a glass syringe (syringe 2) under the conditions tested.

Example 3

Second Set of Stability Tests

Example 3.1

Sample Preparation

Aflibercept from the EU marketed product Eylea® was transferred by 3-step-dialysis into 3 different formulations containing (a) 10 mM histidine/histidine chloride, 40 mM sodium chloride, 5% (w/v) sucrose, 0.03% (w/v) polysorbate 20, pH 6.2 (b) 10 mM histidine/histidine chloride, 40 mM sodium chloride, 5% (w/v) sucrose, 0.03% (w/v) polysorbate 20, pH 6.5 and (c) 10 mM sodium phosphate, 40 mM sodium chloride, 5% (w/v) sucrose, 0.03% (w/v) polysorbate 20, pH 6.2 as shown in Table 9.

Dialyzed aflibercept was adjusted to 40 mg/mL±10% and stored at 5° C., 25° C./60% relative humidity and 40° C./75% relative humidity for up to 3 months in glass vials.

Additionally aflibercept in the different formulations was stressed by five freeze/ thaw cycles.

EU marketed product Eylea® was included in the stability program as control sample (d)—see Table 9.

TABLE 9

| Sample | aflibercept | buffer system | sucrose | sodium chloride | polysorbate 20 | pH |
|---|---|---|---|---|---|---|
| (a) | 40 mg/mL | 10 mM L-histidine/ histidine/HCl | 5% (w/v) | 40 mM | 0.03% (w/v) | pH 6.2 |
| (b) | 40 mg/mL | 10 mM L-histidine/ histidine/HCl | 5% (w/v) | 40 mM | 0.03% (w/v) | pH 6.5 |
| (c) | 40 mg/mL | 10 mM sodium dihydrogen phosphate/ disodium hydrogen phosphate | 5% (w/v) | 40 mM | 0.03% (w/v) | pH 6.2 |
| (d) | | Eylea ® | | | | |

Afterwards the samples according to Table 9 were analyzed by UV-Vis for protein concentration, by size exclusion chromatography (SEC) for the presence of high molecular weight species (HMWS) and by reduced-/ non-reduced sodium dodecyl sulfate polyacrylamide gel electrophoresis (SDS-PAGE) for the presence of fragments and HMWS. Chemical modifications like methionine oxidation and deamidation were quantified by reduced peptide mapping. Alterations of the secondary structure were monitored by FTIR analysis. The activity of aflibercept in the samples was determined by Potency ELISA and by binding to FcRN via biolayer interferometry.

Example 3.2

UV-Vis

During the complete stability program no significant changes in protein concentration (spectrophotometric quantification at 280 nm; n=3) and appearance (visible particles, change in color) was detected in any of the samples.

Example 3.3

Size Exclusion Chromatography

The protein samples of the stability study were loaded onto a TSKgel G3000SWXL, (Tosoh, 300×7.8 mm, 5 µm) column to detect high molecular weight species of aflibercept.

The protein was eluted by isocratic elution using 0.02 M sodium phosphate (pH 6.0) and 0.8 M sodium chloride at a flow rate of 1.0 mL/min at 25° C. Eluted species were detected at a wavelength of 214 nm and displayed on a graph showing the concentration of the eluted species vs. time. The elution profile showed a main peak with the non-aggregated protein and some further peaks of the protein representing higher molecular weight forms of the protein. The area of all peaks was determined. Table 10 shows the percentage of peak area for the aggregates in relation to the total peak area of the eluted species for the samples of Table 9. Each sample was examined in duplicate measurements and the mean value as well as the standard deviation were calculated.

TABLE 10

| Condition | Formulation | HMWS [%] | SD [%] |
|---|---|---|---|
| T0 | (a) | 1.46 | 0.00 |
|  | (b) | 1.51 | 0.00 |
|  | (c) | 1.50 | 0.00 |
|  | (d) | 1.49 | 0.00 |
| 1 M 5° C. | (a) | 1.49 | 0.00 |
|  | (b) | 1.60 | 0.00 |
|  | (c) | 1.49 | 0.01 |
|  | (d) | 1.57 | 0.00 |
| 2 M 5° C. | (a) | 1.59 | 0.04 |
|  | (b) | 1.61 | 0.01 |
|  | (c) | 1.51 | 0.00 |
|  | (d) | 1.62 | 0.04 |
| 3 M 5° C. | (a) | 1.58 | 0.01 |
|  | (b) | 1.78 | 0.11 |
|  | (c) | 1.66 | 0.00 |
|  | (d) | 1.73 | 0.03 |
| 1 M 25° C. | (a) | 1.63 | 0.01 |
|  | (b) | 1.88 | 0.02 |
|  | (c) | 1.81 | 0.01 |
|  | (d) | 2.00 | 0.01 |
| 2 M 25° C. | (a) | 2.03 | 0.00 |
|  | (b) | 2.20 | 0.01 |
|  | (c) | 2.13 | 0.01 |
|  | (d) | 2.46 | 0.01 |
| 3 M 25° C. | (a) | 2.30 | 0.07 |
|  | (b) | 2.78 | 0.06 |
|  | (c) | 2.32 | 0.06 |
|  | (d) | 2.79 | 0.08 |
| 1 M 40° C. | (a) | 13.18 | 0.00 |
|  | (b) | 12.83 | 0.00 |
|  | (c) | 13.32 | 0.00 |
|  | (d) | 13.53 | 0.07 |
| 2 M 40° C. | (a) | 24.69 | 0.02 |
|  | (b) | 24.10 | 0.05 |
|  | (c) | 24.39 | 0.11 |
|  | (d) | 25.29 | 0.10 |
| 3 M 40° C. | (a) | 29.77 | 0.13 |
|  | (b) | 28.40 | 0.33 |
|  | (c) | 29.19 | 0.34 |
|  | (d) | 30.27 | 0.20 |

The generation of HMWS as determined by SEC was comparable between the different formulations for all incubation parameters (temperature, storage time). Both the identity of the higher molecular weight species and the temperature dependent kinetics were comparable between the different samples.

Example 3.4

Non-reduced SDS-PAGE

The non-reduced SDS-PAGE was performed using the conditions described in Example 2.4 with samples stored at each of the storage temperatures for 3 months.

Storing the samples at 5° C. or 25° C./60% relative humidity did not lead to significant changes of the banding pattern in all formulations. In particular, no new impurity bands or a significant increase of existing impurity bands could be detected in all samples shown in Table 9 over the whole incubation period. Storing the samples at 40° C./75% relative humidity led to stronger impurity bands compared to the samples stored at lower temperatures. The results of the non-reduced SDS PAGE analysis of samples incubated at 40° C./75% relative humidity for three months are shown in FIG. 4. Every sample was evaluated as duplicate measurement in the gel.

In the non-reduced SDS-PAGE analysis of all samples incubated for three months at 40° C./75% relative humidity bands representing fragments and higher molecular weight species of aflibercept were visible. The generation of fragments and HMWS during the 3 months incubation was comparable in the kinetics and the identity of the impurities between all tested formulations shown in Table 9.

Example 3.5

Reduced SDS-PAGE

By reduced SDS-PAGE physical modifications such as fragmentation and oligomerization of aflibercept in the different formulations according to Table 9 were determined.

The SDS-PAGE was performed under reducing conditions in a 4-12% Tris-Glycine gel. Samples were pre-diluted to 0.4 mg/ml with water and further diluted to 0.2 mg/ml with SDS sample buffer containing DTT. The samples were incubated at 95° C. for 5 min. After the run the gel was rinsed three times with 100 mL deionized water and dyed with Coomassie overnight at room temperature. After discoloration the gel was scanned and analyzed using QuantityOne Software.

The running conditions were as follows:
voltage: 125 V
current: 35 mA
power: 5W
time: 200 min The non-reduced SDS-PAGE was performed with samples stored at each of the storage temperatures for 3 months.

Storing the samples at 5° C. or 25° C./60% relative humidity did not lead to significant changes of the banding pattern in all formulations. In particular, no generation of new impurity bands or a significant increase of existing impurity bands could be detected in all samples shown in Table 9 over the whole incubation period. Storing the samples at 40° C./75% relative humidity led to stronger impurity bands compared to the samples stored at lower temperatures. These impurity bands were comparable between all tested formulations shown in Table 9 in both the kinetics and the identity of the impurities. The results of the reduced SDS PAGE analysis of samples incubated for three months at 40° C./75% relative humidity are shown in FIG. 5.

Example 3.6

FTIR

FTIR (Fourier transform infrared spectroscopy) spectroscopy provides information on the secondary structure of proteins and works by excitation of a sample with infrared radiation and detection of the wavelengths absorbed by the protein.

Each protein has a characteristic set of absorption bands in its infrared spectrum. Characteristic bands found in the infrared spectra of proteins and polypeptides include the Amide I and Amide II region. These arise from the peptide bonds that link the amino acids in the protein backbone. The Amide I band was evaluated in this assay to monitor the secondary structure components alpha helices and beta sheets.

Samples from the stability studies were diluted with their corresponding formulation without aflibercept (placebo formulation) to a concentration of 10 mg/mL aflibercept and analyzed by a FTIR Tensor27 from Bruker Optics in an AquaSpec cell from Micro Biolytics. Data analysis was performed with Opus 6.5 software (Bruker Optics). 10 measurements were performed with an injection volume of 2.0 µl and the second derivative spectra were analyzed in the Amide I absorption area from 1700-1600 cm$^{-1}$. Analysis of the formulations without aflibercept served as background measurements and the signals were subtracted from the protein spectra.

Device setting for FTIR
Resolution: 4 cm$^{-1}$
Sample Scan Time: 30 scans
Background Scan Time: 30 scans
Result spectrum: Absorbance
Source Setting: MIR
Beamsplitter: KBr
Detector Setting: LN-MCT Photovoltaic 12 H
Scanner Velocity: 20 kHz
Water batch: 25° C.

The analysis of the aflibercept containing formulations shown in Table 9 by FTIR with regard to secondary structure did not reveal any alteration during the complete stability program. All samples showed a comparable constant percentage of about 10% alpha helicesand 40% beta-sheets.

Example 3.7

Reduced Peptide Mapping

By reduced peptide mapping the purity of aflibercept with regard to asparagine deamidation and methionine oxidation was analyzed for all formulations of Table 9 which were stored at different temperatures for three months or subjected to five freeze/thaw cycles. The conditions for the analysis were the same as those used in example 2.6.

5 oxidated methionines in aflibercept could be identified (AA 20; AA 163; AA 192, AA 237, AA 413) and were summed up for evaluation of the total methionine oxidation (see Table 11). 5 deamidations of asparagine could be identified (AA 84; AA 91; AA 99; AA 271; AA 300) and were summed up for evaluation of the total deamidation (see Table 11)

TABLE 11

| Condition | Formulation | Total methionine oxidations [%] | Total deamidations [%] |
|---|---|---|---|
| T0 | (a) | 22.1 | 33.3 |
|  | (b) | 21.3 | 29.7 |
|  | (c) | 25.1 | 31.0 |
|  | (d) | 24.0 | 30.8 |
| 3 M 5° C. | (a) | 23.6 | 32.4 |
|  | (b) | 21.8 | 31.2 |
|  | (c) | 24.1 | 32.4 |
|  | (d) | 23.3 | 31.6 |
| 3 M 25° C. | (a) | 24.3 | 40.0 |
|  | (b) | 25.2 | 46.2 |
|  | (c) | 27.1 | 39.2 |
|  | (d) | 23.8 | 37.9 |
| 3 M 40° C. | (a) | 27.4 | 87.6 |
|  | (b) | 24.6 | 102.2 |
|  | (c) | 29.5 | 87.1 |
|  | (d) | 25.0 | 102.2 |
| 5 × F/T | (a) | 21.1 | 32.4 |
|  | (b) | 19.1 | 30.5 |
|  | (c) | 24.4 | 34.1 |
|  | (d) | 22.5 | 33.6 |

The formulations shown in Table 9 showed a comparable stability with regard to methionine oxidation and deamidation of asparagine. Whereas at all temperature conditions only slight increases of methionine oxidation in the different formulations were detected, the increase of deamidations was significantly temperature-dependent. All aflibercept-containing formulations of Table 9 showed a comparable increase of deamidations when stored for 3 months at 25° C./60% relative humidity or 40° C./75% relative humidity. Freeze/ thaw did not show an influence on both methionine oxidation and asparagine deamidations in all tested formulations.

Example 3.8

Relative Potency

The relative potency of aflibercept was determined by an ELISA (enzyme linked immunosorbent assay) which is based on the binding of aflibercept to Vascular Endothelial Growth Factor (VEGF).

All test samples were diluted to an assay concentration of 1.7 pM aflibercept with StartingBlock (PBS) Blocking Buffer (Thermo Fisher, No. 37538), mixed with VEGF-A165 (2.5 ng/mL assay concentration) and incubated overnight at 4° C. 100 µl of the samples were transferred to a microtiter plate coated with an anti-VEGF antibody. Non-neutralized VEGF bound to the coated anti-VEGF antibody in the microtiter-well, while complexes of aflibercept/VEGF were removed by three washing steps (each 300 µl) with PBS/ 0.1% (w/v) polysorbate 20. The microtiter plate was sealed with an adhesive foil and incubated for 15 minutes at room temperature with adequate shaking. After additional washing steps (3×300 µl PBS/0.1% (w/v) polysorbate 20) the binding of VEGF was detected by addition of a biotinylated polyclonal anti-VEGF 165 antibody (100 µl of a 200 µg/mL solution), sealing, incubation for further 120 minutes in the dark and visualized using a Streptavidin-HRP (Horseradish peroxidase) conjugate via the oxidation of 3,3',5,5'-tetramethylbenzidine (TMB). The colorimetric reaction was stopped after 20 minutes incubation in the dark by adequate shaking with sulphuric acid, the absorption was measured at a wavelength of 450 nm with a Fluorescence reader for microtiter plates (Tecan Infinite M200 Pro) and compared to an aflibercept standard.

All test samples were analyzed as duplicates.

During the 3 months incubation at 5° C. and 25° C./60% relative humidity no significant loss of the relative potency could be detected in all formulations shown in Table 9 compared to the starting material. Also freeze/ thaw cycles did not influence the relative potency of aflibercept in each of the tested formulations. Incubation at 40° C./75% relative humidity for three months led to a comparable decrease of the relative potency in all formulations.

Example 3.9

Binding to FcRN

The evaluation of the kinetic parameters (KD, $k_{on}$, $k_{dis}$) using Bio-Layer Interferometry technology ((Pall-FortéBIO Octet RED 96) for the interaction between the neonatal Fc receptor (FcRn) and aflibercept in the formulations shown in Table 9 during the stability assays showed a similar picture.

Bio-Layer Interferometry (BLI) is a label-free technology for measuring biomolecular interactions. It is an optical analytical technique that analyzes the interference pattern of white light reflected from two surfaces: a layer of immobilized protein on the biosensor tip and an internal reference layer. The binding between HIS-tagged neonatal Fc receptor (FcRn, No. CT009-H08H from Sino Biological Inc) immobilized on the surface of Ni-NTA biosensors coated with nickel-charged Tris-NTA (No. 18-5101 from Pall-FortéBIO)

and aflibercept produces an increase in optical thickness at the biosensor tip, which results in a wavelength shift, which is a direct measure of the change in thickness of the biological layer and provides the ability to determine binding specificity and rates of association and dissociation.

Samples from Table 9 were analyzed after 3 months incubation at 5° C. and 40° C./75% relative humidity and compared to the starting material. The samples were diluted with their corresponding formulation without aflibercept (placebo formulation) to 10 mg/mL aflibercept and further diluted to 0.704 µg/mL, 0.352 µg/mL and 0.176 µg/mL aflibercept with kinetic buffer (DPBS/0.05% (w/v) BSA/0.02% (w/v) polysorbate 20/0.5 M sodium chloride, pH 6.0). Ni-NTA biosensors were hydrated with 200 µl kinetic buffer. Each well was filled with 200 µl of kinetic buffer, ligand solution and analyte solution according to following scheme in Table 12:

TABLE 12

| | Baseline 1/7 | Ligand [mg/mL] 2/8 | Baseline 2 3/9 | Baseline 3 + Dissociation 4/10 | Aflibercept [mg/mL] 5/11 |
|---|---|---|---|---|---|
| A | Kinetic buffer | 1.0 | Kinetic buffer | Kinetic buffer | 0.704 |
| B | Kinetic buffer | 1.0 | Kinetic buffer | Kinetic buffer | 0.352 |
| C | Kinetic buffer | 1.0 | Kinetic buffer | Kinetic buffer | 0.176 |
| D | Kinetic buffer | 1.0 | Kinetic buffer | Kinetic buffer | Kinetic buffer |

Kinetic buffer was pipetted into row D instead of analyte to serve as reference. Measurement parameters:

Plate temperature: 30° C.

Shaking speed: 1000 rpm

Acquisition rate: Standard kinetics (5.0 Hz averaging by 20)

The signal of the sample was recorded according to Table 13:

TABLE 13

| No. | Step | Time [sec.] | Sample column |
|---|---|---|---|
| 1 | Baseline | 300 | 1/7 |
| 2 | Loading | 600 | 2/8 |
| 3 | Baseline 2 | 150 | 3/9 |
| 4 | Baseline 3 | 150 | 4/10 |
| 5 | Assiciation | 400 | 5/11 |
| 6 | Dissociation | 2400 | 4/10 |

The data were analyzed with the Octet Data Analysis software resulting in the kinetic parameters $K_D$, $k_{on}$ and $k_{dis}$ values.

TABLE 14

| Condition | Formulation | $K_D$ | $k_{on}$ | $k_{dis}$ |
|---|---|---|---|---|
| T0 | (a) | 1.18E-10M | 5.56E+05 1/M * s | 6.56E-05 1/s |
| | (b) | 1.06E-11M | 6.13E+05 1/M * s | 6.47E-05 1/s |
| | (c) | 1.07E-10M | 6.05E+05 1/M * s | 6.44E-05 1/s |
| | (d) | 9.93E-11M | 5.60E+05 1/M * s | 5.56E-05 1/s |
| 3 M 5° C. | (a) | 9.80E-11M | 5.96E+05 1/M * s | 5.84E-05 1/s |
| | (b) | 9.23E-11M | 6.19E+05 1/M * s | 5.71E-05 1/s |
| | (c) | 1.03E-10M | 6.10E+05 1/M * s | 6.28E-05 1/s |
| | (d) | 9.68E-11M | 6.31E+05 1/M * s | 6.11E-05 1/s |

TABLE 14-continued

| Condition | Formulation | $K_D$ | $k_{on}$ | $k_{dis}$ |
|---|---|---|---|---|
| 3 M 40° C. | (a) | 9.05E-11M | 4.54E+05 1/M * s | 4.11E-05 1/s |
| | (b) | 5.91E-11M | 4.83E+05 1/M * s | 2.86E-05 1/s |
| | (c) | 5.91E-11M | 4.59E+05 1/M * s | 2.71E-05 1/s |
| | (d) | 6.09E-11M | 4.93E+05 1/M * s | 3.00E-05 1/s |

The kinetic parameters ($K_D$, $k_{on}$ and $k_{off}$) were similar to the starting conditions after 3 months of incubation at 5° C. for all formulations. Storing the samples for 3 months at 40° C./75% relative humidity led to a decrease of $K_D$ which was mainly due to the decreased dissociation rate $k_{dis}$. This decrease was comparable for all tested formulations of Table 9.

In summary, no significant differences between the formulations shown in Table 9 could be detected both with regard to physical and chemical stability when stored for 3 months at 5° C., 25° C./60% relative humidity and 40° C./75% relative humidity or treated by freeze/thaw cycles, also the trend in biological activity did not differ between the formulations. From the results shown it is apparent that the stability of aflibercept in the histidine-based formulations of the present invention (a and b) is at least comparable with the stability in the formulation of the phosphate-buffered formulation (c) or the EU marketed Eylea® under the conditions tested.

The invention claimed is:

1. A method of treating an intraocular neovascular disease comprising administering a liquid pharmaceutical composition consisting of histidine hydrochloride/L-histidine, polysorbate 20, NaCl, aflibercept, sucrose and water and having a pH from 6.2 to 6.5.

2. The method of claim 1, wherein histidine hydrochloride/L-histidine is present in a concentration of from 1 mM to 40 mM.

3. The method of claim 1, wherein the polysorbate 20 is present in a concentration of from 0.01 to 0.08% (w/v).

4. The method of claim 3, wherein the polysorbate 20 is present in a concentration of 0.03% (w/v).

5. The method of claim 1, wherein the NaCl is present in a concentration of from 20 to 100 mM.

6. The method of claim 5, wherein the NaCl is present in a concentration of 40 mM.

7. The method of claim 1, wherein the aflibercept is present in a concentration of 6 to 45 mg/ml.

8. The method of claim 1, wherein the sucrose is present in a concentration of 3-20% (w/v).

9. The method of claim 8, wherein the sucrose is present in a concentration of 5% (w/v).

10. The method of claim 1, wherein the liquid pharmaceutical composition consists of 10 mM histidine hydrochloride/L-histidine, 0.03% polysorbate 20 (w/v), 40 mM NaCl, 40 mg/ml aflibercept, 5% sucrose and water and having a pH from 6.2 to 6.5.

11. The method of claim 10, wherein the intraocular neovascular disease is age-related macular degeneration (AMD), visual impairment due to diabetic macular oedema (DME), visual impairment due to macular oedema secondary to retinal vein occlusion (branch RVO or central RVO), or visual impairment due to choroidal neovascularisation (CNV) secondary to pathologic myopia.

12. The method of claim 10, wherein the pharmaceutical composition is administered by intravitreal injection.

13. The method of claim 1, wherein the intraocular neovascular disease is age-related macular degeneration (AMD), visual impairment due to diabetic macular oedema (DME), visual impairment due to macular oedema secondary to retinal vein occlusion (branch RVO or central RVO), or visual impairment due to choroidal neovascularisation (CNV) secondary to pathologic myopia.

14. The method of claim 1, wherein the pharmaceutical composition is administered by intravitreal injection.

\* \* \* \* \*